United States Patent
Beck et al.

(10) Patent No.: US 10,704,029 B2
(45) Date of Patent: Jul. 7, 2020

(54) **MUTANT 3-HYDROXYBUTYRATE DEHYDROGENASE FROM *RHODOBACTER SPHAEROIDES* AS WELL AS METHODS AND USES INVOLVING THE SAME**

(71) Applicants: Roche Diagnostics Operations, Inc., Indianapolis, IN (US); Roche Diabetes Care, Inc., Indianapolis, IN (US)

(72) Inventors: Daniela Beck, Penzberg (DE); Mara Boenitz-Dulat, Tutzing (DE); Peter Kratzsch, Penzberg (DE); Thomas Streidl, Seeshaupt (DE); Carina Horn, Biblis (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 135 days.

(21) Appl. No.: 16/059,096

(22) Filed: Aug. 9, 2018

(65) Prior Publication Data

US 2018/0346886 A1 Dec. 6, 2018

Related U.S. Application Data

(63) Continuation of application No. PCT/EP2017/052855, filed on Feb. 9, 2017.

(30) Foreign Application Priority Data

Feb. 9, 2016 (EP) ..................................... 16000321

(51) Int. Cl.
| | | |
|---|---|---|
| *C12N 9/02* | (2006.01) | |
| *C12N 9/04* | (2006.01) | |
| *C12Q 1/32* | (2006.01) | |
| *C12P 7/18* | (2006.01) | |

(52) U.S. Cl.
CPC ............. *C12N 9/0006* (2013.01); *C12P 7/18* (2013.01); *C12Q 1/32* (2013.01); *C12Y 101/0103* (2013.01)

(58) Field of Classification Search
CPC .................. C12N 9/0006; C12Y 101/0103
See application file for complete search history.

(56) References Cited

U.S. PATENT DOCUMENTS

| | | | |
|---|---|---|---|
| 4,816,224 A | 3/1989 | Vogel et al. | |
| 5,413,690 A | 5/1995 | Kost et al. | |
| 5,762,770 A | 6/1998 | Pritchard et al. | |
| 5,801,006 A | 9/1998 | Kaufman | |
| 5,997,817 A | 12/1999 | Crismore et al. | |
| 6,255,093 B1 | 7/2001 | Schmuck et al. | |
| 6,541,216 B1 | 4/2003 | Wilsey et al. | |
| 9,266,109 B2 | 2/2016 | Howell et al. | |
| 10,508,267 B2* | 12/2019 | Kratzsch | C12N 9/0006 |
| 2011/0212503 A1 | 9/2011 | Yamaguchi et al. | |
| 2014/0124384 A1 | 5/2014 | Gerber et al. | |

FOREIGN PATENT DOCUMENTS

| | | |
|---|---|---|
| DE | 19815685 A1 | 10/1999 |
| DE | 102007035109 A1 | 1/2009 |
| EP | 0262445 A1 | 4/1988 |
| JP | 8070856 A | 3/1996 |
| KR | 2015/0093557 A | 8/2015 |
| WO | 1998/033936 A1 | 8/1998 |
| WO | 2001/046457 A2 | 6/2001 |
| WO | 2001/094370 A1 | 12/2001 |
| WO | 2006/040172 A1 | 4/2006 |
| WO | 2007/012494 A1 | 2/2007 |
| WO | 2007/118647 A1 | 10/2007 |
| WO | 2009060432 A1 | 5/2009 |
| WO | 2011/012270 A1 | 2/2011 |
| WO | 2014/068024 A1 | 5/2014 |
| WO | 2014/195363 A1 | 12/2014 |
| WO | 2017/109003 A1 | 6/2017 |

OTHER PUBLICATIONS

Anderson, Bruce M., Analogs of Pyridine Nucleotide Coenzymes, The Pyridine Nucleotide Coenzymes, 1982, pp. 91-133, Ch. 4, Academic Press, Inc., New York.
Database EMBL, SubName: Full=3-hydroxybutyrate dehydrogenase, Retrived from UniPro EMBL A0A0N9NPT3, 2016, 1 p.
Database EMBL, SubName: Full=D-beta-hydroxybutyrate dehydrogenase, Retrieved from UniProt A0A0D6B253, 2015, 1 p.
Database UNIPROT, Castellaniella defragrans 65Phen D-beta-hydroxybutyrate dehydrogenase—sequence, Retrieved from EBI Accession No. UNIPROT:W8X517, 2014, 2 pp.
Database UNIPROT, Castellaniella defragrans 65Phen; Bacteria, Retrieved from EBI Accession No. UNIPROT:W8X517 CASDE, 2014, 1 p.
Database UNIPROT, SubName: Full=3-hydroxybutyrate dehydrogenase, Retrieved from EBI Accession No. UNIPROT A0A0L8EMR0, 2015, 1 p.
International Search Report dated May 15, 2017, in Application No. PCT/EP2017/052855, 3 pp.
Lillis, B. et al., Investigation into immobilisation of lactate oxidase to improve stability, Sensors and Actuators B, 2000, pp. 109-114, vol. 68.
Oppenheimer, Norman J., Chemistry and Solution Conformation of the Pyridine Coenzymes, The Pyridine Nucleotide Coenzymes, 1982, pp. 51-89, Ch. 3, Academic Press, Inc., New York.
Petasch, Jan et al., The oxygen-independent metabolism of cyclic monoterpenes in Castellaniella defragrans 65Phen, BMC Microbiology, 2014, 13 pp., vol. 14, No. 164.

(Continued)

*Primary Examiner* — Tekchand Saidha
(74) *Attorney, Agent, or Firm* — Dinsmore & Shohl LLP

(57) ABSTRACT

The present invention relates to a mutant 3-hydroxybutyrate dehydrogenase (3-HBDH) with improved performance relative to the wild-type 3-HBDH, a nucleic acid encoding the mutant 3-HBDH, a cell comprising the mutant 3-HBDH or the nucleic acid, a method of determining the amount or concentration of 3-hydroxybutyrate in a sample, and a device for determining the amount or concentration of 3-hydroxybutyrate in a sample.

20 Claims, No Drawings

Specification includes a Sequence Listing.

(56) References Cited

OTHER PUBLICATIONS

Yeon, Young Joo et al., Enzymatic reduction of levulinic acid by engineering the substrate specificity of 3-hydroxybutyrate dehydrogenase, Bioresource Technology, 2013, pp. 377-380, vol. 134.

* cited by examiner

MUTANT 3-HYDROXYBUTYRATE DEHYDROGENASE FROM *RHODOBACTER SPHAEROIDES* AS WELL AS METHODS AND USES INVOLVING THE SAME

The present invention relates to a mutant 3-hydroxybutyrate dehydrogenase (3-HBDH) with improved performance relative to the wild-type 3-HBDH, a nucleic acid encoding the mutant 3-HBDH, a cell comprising the mutant 3-HBDH or the nucleic acid, a method of determining the amount or concentration of 3-hydroxybutyrate in a sample and a device for determining the amount or concentration of 3-hydroxybutyrate in a sample.

Ketone bodies are produced in the liver, mainly from the oxidation of fatty acids, and are exported to peripheral tissues for use as an energy source. They are particularly important for the brain, which has no other substantial non-glucose-derived energy source. The two main ketone bodies are 3-hydroxybutyrate and acetoacetate. Biochemically, abnormalities of ketone body metabolism can be subdivided into three categories: ketosis, hypoketotic hypoglycemia, and abnormalities of the 3-hydroxybutyrate/acetoacetate ratio.

An abnormal elevation of the 3-hydroxybutyrate/acetoacetate ratio usually implies a non-oxidized state of the hepatocyte mitochondrial matrix resulting from hypoxia-ischemia or other causes.

The presence of ketosis normally implies that lipid energy metabolism has been activated and that the entire pathway of lipid degradation is intact. In rare cases, ketosis reflects an inability to utilize ketone bodies. Ketosis is normal during fasting, after prolonged exercise, and when a high-fat diet is consumed. During the neonatal period, infancy and pregnancy, times at which lipid energy metabolism is particularly active, ketosis develops readily.

Pathologic causes of ketosis include diabetes, ketotic hypoglycemia of childhood, corticosteroid or growth hormone deficiency, intoxication with alcohol or salicylates, and several inborn errors of metabolism.

The formation of ketone bodies is increased when lipolysis is increased e.g. in insulin deficiency (diabetes mellitus; in particular type I diabetics), when the glucagon concentration is increased and in a fasting state. In such cases the normal physiological concentration of less than 7 mg/dl can increase to more than 10-fold. Over the past years 3-hydroxybutyrate has proven to be an extremely reliable parameter for monitoring an insulin therapy.

The absence of ketosis in a patient with hypoglycemia is abnormal and suggests the diagnosis of either hyperinsulinism or an inborn error of fat energy metabolism.

Accordingly, ketone bodies are an interesting diagnostic target, particularly for diabetes. Therefore, there is an ongoing need for robust and sensitive test-systems for ketone bodies, especially 3-hydroxybutyrate. The ratio of 3-hydroxybutyrate to acetone or acetoacetic acid is normally 3:1. In keto-acidoses the ratio increases to 6:1 to 12:1. A suitable 3-HBDH should enable the development of a quantitative test for 3-hydroxybutyrate.

Surprisingly, it has been found that a variety of mutants of the 3-hydroxybutyrate dehydrogenase from *Rhodobacter sphaeroides* show improved performance, particularly increased thermal stability and/or affinity for substrate and/or cofactor. As shown in the Examples, there are many sites at the wild-type enzyme which allow for mutations, which increase thermal stability and/or affinity for substrate and/or cofactor of the mutant relative to the wild-type enzyme.

The inventors identified a considerable amount of amino acids in the wild-type 3-HBDH, the substitutions of which increased the performance of the resulting mutants relative to the wild-type HBDH (see e.g. Table 1A and 1B of the Examples). Particularly, amino acids may be substituted to increase thermal stability and optionally affinity for substrate and/or cofactor (for 3-hydroxybutyrate and/or NAD or derivatives of NAD, e.g. carba-NAD). Suitable examples of those sites include positions 66, 109 113, 125, 140, 144, 145, 195, 197, 217, 223, 232, 239, 250 and/or 257 of SEQ ID NO: 1. The performance of the mutant 3-HBDH could be further increased by combining mutations at the above or further sites (see Tables 2A and 2B). Particularly suitable examples of those mutants include those with the mutations (for definitions of abbreviations see below)

125Phe;
144Arg;
232Cys;
250Met;
230Leu and 250Met;
37Tyr and 250Met;
37Tyr, 230Leu and 250Met;
202Gly, 230Leu and 250Met;
37Tyr, 145Gly, 230Leu and 250Met; or
37Tyr, 195Gln, 230Leu and 250Met
(see Examples).

Accordingly, in a first aspect, the present invention relates to a mutant 3-hydroxybutyrate dehydrogenase (3-HBDH) from *Rhodobacter sphaeroides* with improved performance relative to the wild-type 3-HBDH. Preferably, the mutant 3-3-HBDH from *Rhodobacter sphaeroides* with improved performance relative to the wild-type 3-HBDH comprises an amino acid sequence that is at least 80% identical to the amino acid sequence of SEQ ID NO: 1 (3-HBDH from *Rhodobacter sphaeroides*; wild-type 3-HBDH) and has at least one amino acid substitution relative to the wild-type 3-HBDH at a position corresponding to position 250 of SEQ ID NO: 1. More preferably, the amino acid at the position corresponding to position 250 of SEQ ID NO: 1 is substituted with Met (250Met) or Ile (250Ile), particularly with Met (250Met). The position and substitutions have been proven to be advantageous in order to improve performance of a mutant 3-HBDH (see Tables 1A and 1B) and may be combined with further mutations (see Tables 2A and 2B). Accordingly, particularly suitable mutants include those with the mutations 250Met;
230Leu and 250Met;
37Tyr and 250Met;
37Tyr, 230Leu and 250Met;
202Gly, 230Leu and 250Met;
37Tyr, 145Gly, 230Leu and 250Met; or
37Tyr, 195Gln, 230Leu and 250Met
(see Examples).

3-Hydroxybutyrate dehydrogenase (3-HBDH) (EC 1.1.1.30) belongs to the family of oxidoreductases, to be specific is an enzyme that catalyzes the stereospecific oxidation of 3-hydroxybutanoate/3-hydroxybutyrate/(R)-3-hydroxybutyrate/3-hydroxybutyric acid (3-HB) to acetoacetate with NAD or derivatives as cofactor:

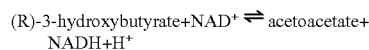
(R)-3-hydroxybutyrate+NAD$^+$ ⇌ acetoacetate+ NADH+H$^+$

The systematic name of this enzyme class is (R)-3-hydroxybutanoate:NAD$^+$ oxidoreductase. Other names in common use include NAD$^+$-beta-hydroxybutyrate dehydrogenase, hydroxybutyrate oxidoreductase, beta-hydroxybutyrate dehydrogenase, D-beta-hydroxybutyrate dehydrogenase, D-3-hydroxybutyrate dehydrogenase, D-(−)-3-hydroxybutyrate dehydrogenase, beta-hydroxybutyric acid dehydrogenase, 3-D-hydroxybutyrate dehydrogenase, and beta-hydroxybutyric dehydrogenase. This enzyme participates in synthesis and degradation of ketone bodies and butanoate metabolism and it may be used in order to determine ketone bodies in samples, such as a blood sample.

The term "wild-type 3-HBDH" relates to a 3-HBDH as it typically occurs in nature. A wild-type 3-HBDH from the purple photosynthetic bacterium *Rhodobacter sphaeroides* was cloned in *E. coli* and further described in 1999 (DE 19815685 A1). However, the enzyme is characterized by a rather low stability (resulting in short storage life), which is disadvantageous in biotechnical, biomedical and diagnostic applications. Particularly, the short storage life has a negative impact on applicability of the enzyme, if the use of a previously prepared enzyme is intended. This includes particularly commercial products such as enzyme preparations, kits, test strips etc, which are usually prepared in large scale, stored and then marketed e.g. in smaller batches. Additionally, it is evidently desirable to increase the enzyme's affinity for the substrates and/or cofactors. Increased affinity and/or stability will increase the performance of the enzyme in biotechnical applications and devices. The commonly accepted amino acid sequence of the typically occurring wild-type 3-HBDH of *Rhodobacter sphaeroides* is given below as SEQ ID NO:1.

The term "mutant 3-hydroxybutyrate dehydrogenase (3-HBDH) from *Rhodobacter sphaeroides*" relates to a 3-HBDH enzyme whose amino acid sequence differs from the wild-type 3-HBDH from *Rhodobacter sphaeroides*, particularly the amino acid sequence of SEQ ID NO:1, by at least one mutation, i.e. one or more amino acid substitutions, additions, deletions or combinations thereof, particularly by at least one substitution.

The term "with improved performance relative to the wild-type 3-HBDH" means that the performance of the mutant enzyme is improved relative to the wild-type 3-HBDH from *Rhodobacter sphaeroides*. The performance is improved, if the mutant enzyme has a higher performance, e.g. higher activity in converting 3-HB into acetoacetate, at any condition (e.g. after storage, at a particular pH, with a specific buffer, at a chosen temperature, with a particular cofactor (e.g. carba-NAD), at a specific substrate or cofactor concentration etc). Higher performance may be especially increased stability (such as thermal stability) and/or affinity for one or more substrates/cofactors (e.g. carba-NAD and/or 3-HB). Preferably, the performance is improved, if the mutant enzyme, e.g., has a higher relative remaining activity in converting 3-HB into acetoacetate, upon being stressed with given conditions (e.g. storage, buffer conditions, temperature, concentration of cofactor or substrate) compared to the activity without being stressed under these conditions and/or if the mutant enzyme, e.g., has a higher relative activity (i.e. activity at a subsaturation concentration/activity at a saturation concentration).

The sequence of the wild-type 3-HBDH from *Rhodobacter sphaeroides* is shown as SEQ ID NO: 1:

```
(3-HBDH from Rhodobacter sphaeroides)
                                                          SEQ ID NO: 1
MDLNGKRAIV TGSNSGIGLG CAEELARAGA EVVINSFTDR DEDHALAEKI GREHGVSCRY    60

IAADMSDGEA CRALIETAGG CDILVNNAGI QHVSSIEEFP VGKWNAILAI NLSSAFHTTA   120

AALPGMRAKG WGRIVNIASA HGLTASPYKS AYVAAKHGVV GFTKVTALET AGKGITCNAI   180

CPGYVLTPLV EAQIPDQMKA HDMDRETVIR EVMLDRQPSR QFATTGQIGG TVVFLCSGAA   240

DQITGTTISV DGGWTAL                                                  257
```

Accordingly, a preferred example of a naturally occurring wild-type 3-HBDH is given above as SEQ ID NO: 1.

If one or more mutations are introduced into the wild-type sequence, especially the sequence of SEQ ID NO: 1, a mutant 3-HBDH is obtained. With respect to the mutant 3-HBDH of the present invention it is noted that the mutant is functionally active and shows improved performance relative to the wild-type 3-HBDH. This means that the mutant has maintained its enzymatic function of conversion of 3-HB into acetoacetate. Additionally, preferably at least the stability and optionally the enzyme's affinity for the substrate and/or cofactors is increased. The mutant differs from the wild-type 3-HBDH by one or more amino acid substitutions, additions and/or deletions, especially at least one or more substitutions.

The sequence of the mutant 3-HBDH according to the present invention comprises (optionally in addition to the substitutions specified herein) one or more amino acid substitution(s), deletion(s) or addition(s), especially one or more substitutions, particularly one or more conservative amino acid substitutions.

In one embodiment of the present invention, the mutant 3-HBDH according to the present invention may comprise one or more amino acid substitution(s), particularly a limited number of substitutions (e.g. up to 50, 40, 30, 20 especially 10 amino acid substitutions). Suitable substitutions are given in the Examples, particularly in the Tables. All the substitutions identified in the Examples as suitable in order to increase performance of 3-HBDH may be used in the invention either alone or in combination with each other and/or with further substitutions, e.g. conservative substitutions. "Conservative amino acid substitution" refers to a substitution of a residue with a different residue having a similar side chain, and thus typically involves substitution of the amino acid in the polypeptide with amino acids within the same or similar defined class of amino acids. By way of example and not limitation, an amino acid with an aliphatic side chain may be substituted with another aliphatic amino acid, e.g., alanine, valine, leucine, and isoleucine; an amino acid with hydroxyl side chain is substituted with another amino acid with a hydroxyl side chain, e.g., serine and threonine; an amino acid having aromatic side chains is substituted with another amino acid having an aromatic side chain, e.g., phenylalanine, tyrosine, tryptophan, and histidine; an amino acid with a basic side chain is substituted with another amino acid with a basic side chain, e.g., lysine and arginine; an amino acid with an acidic side chain is substituted with another amino acid with an acidic side chain, e.g., aspartic acid or glutamic acid; and a hydrophobic or hydrophilic amino acid is replaced with another hydrophobic or hydrophilic amino acid, respectively. Examples of conservative amino acid substitutions include those listed below:

| Original Residue | Conservative Substitutions |
| --- | --- |
| Ala, Leu, Val, Ile | Other aliphatic (Ala, Leu, Val, Ile) |
| | Other non-polar (Ala, Leu, Val, Ile, Gly, Met) |
| Gly, Met | Other non-polar (Ala, Leu, Val, Ile, Gly, Met) |
| Asp, Glu | Other acidic (Asp, Glu) |
| Lys, Arg | Other basic (Lys, Arg) |
| Asn, Gln, Ser, Thr | Other polar (Asn, Gln, Ser, Thr) |
| His, Tyr, Trp, Phe | Other aromatic (His, Tyr, Trp, Phe) |
| Cys, Pro | None |

In one embodiment of the present invention, the mutant 3-HBDH according to the present invention may comprise one or more amino acid addition(s), particularly small (e.g. up to 50, 40, 30, 20 especially 10 amino acids) internal amino acid additions. Alternatively, additions may be achieved by combining the mutant 3-HBDH into a fusion protein comprising the mutant 3-HBDH of the present invention.

Fusion proteins are proteins created by joining of two or more originally separate proteins or peptides. This procedure results in a polypeptide with functional properties derived from each of the original proteins. Accordingly, depending on the intended use of the 3-HBDH it may be combined with a further peptide or protein into a fusion protein. The proteins may be fused via a linker or spacer, which increases the likelihood that that the proteins fold independently and behave as expected. Especially in the case where the linkers enable protein purification, linkers in protein or peptide fusions are sometimes engineered with cleavage sites for proteases or chemical agents that enable the liberation of the two separate proteins. Di- or multimeric fusion proteins can be manufactured through genetic engineering by fusion to the original proteins of peptide domains that induce artificial protein di- or multimerization (e.g., streptavidin or leucine zippers). Fusion proteins can also be manufactured with toxins or antibodies attached to them. Other fusions include the addition the addition of signal sequences, such a lipidation signal, sequence, a secretion signal sequence, a glycosylation signal sequence, a translocation signal peptide etc.

Preferably, the fusion protein of the present invention comprises a tag. Tags are attached to proteins for various purposes, e.g. in order to ease purification, to assist in the proper folding in proteins, to prevent precipitation of the protein, to alter chromatographic properties, to modify the protein or to mark or label the protein. Examples of tags include Arg-tag, the His-tag, the Strep-tag, the Flag-tag, the T7-tag, the V5-peptide-tag, the GST-tag and the c-Myc-tag.

In one embodiment of the present invention, the mutant 3-HBDH according to the present invention may comprise one or more amino acid deletion(s), particularly N- and/or C-terminal deletions. The deletions may be small (e.g. up to 50, 40, 30, 20, especially 10 amino acids).

In another embodiment, the sequence of the mutant 3-HBDH according to the present invention may comprise, preferably in addition to the substitutions specified herein, a combination of one or more deletion(s), substitution(s) or addition(s) as defined above.

In a preferred embodiment of the present invention, the mutant 3-HBDH comprises an amino acid sequence that is at least 80% identical to the amino acid sequence of SEQ ID NO: 1 (3-HBDH from *Rhodobacter sphaeroides*; wild-type 3-HBDH).

The term "at least 80% identical" or "at least 80% sequence identity" as used herein means that the sequence of the mutant 3-HBDH according to the present invention has an amino acid sequence characterized in that, within a stretch of 100 amino acids, at least 80 amino acids residues are identical to the sequence of the corresponding wild-type sequence. Sequence identities of other percentages are defined accordingly.

Sequence identity according to the present invention can, e.g., be determined by methods of sequence alignment in form of sequence comparison. Methods of sequence alignment are well known in the art and include various programs and alignment algorithms which have been described in, e.g., Pearson and Lipman (1988). Moreover, the NCBI Basic Local Alignment Search Tool (BLAST) is available from several sources, including the National Center for Biotechnology Information (NCBI, Bethesda, Md.) and on the internet, for use in connection with the sequence analysis programs blastp, blastn, blastx, tblastn and tblastx. Percentage of identity of mutants according to the present invention relative to the amino acid sequence of e.g. SEQ ID NO: 1 is typically characterized using the NCBI Blast blastp with standard settings. Alternatively, sequence identity may be determined using the software GENEious with standard settings. Alignment results can be, e.g., derived from the Software Geneious (version R8), using the global alignment protocol with free end gaps as alignment type, and Blosum62 as a cost matrix.

As detailed above, the mutant 3-HBDH of the present invention in one embodiment comprises an amino acid sequence that is at least 80% identical to the amino acid sequence of SEQ ID NO: 1. In a preferred embodiment, the mutant 3-HBDH comprises or consists of an amino acid sequence which is at least 85%, 90%, 95%, 96%, 97%, 98%, or 99% identical to any of the amino acid sequences of SEQ ID NO: 1. Sequence identity may be determined as described above.

In another preferred embodiment the mutant of the present invention has at least one amino acid substitution relative to the wild-type 3-HBDH, wherein the at least one amino acid substitution is at one or more of the position(s) corresponding to position(s) 66, 109, 113, 125, 140, 144, 145, 195, 197, 217, 223, 232, 239, 250 and/or 257 of SEQ ID NO: 1, particularly at least position(s) 125, 144, 232 and/or 250 of SEQ ID NO: 1, more particularly at least position(s) 125, 144, and/or 250 of SEQ ID NO: 1, especially at least position 250 of SEQ ID NO: 1. It has been shown in the Examples that substitution of the amino acid at the position corresponding to the above positions of SEQ ID NO: 1 increases stability and/or affinity for the substrates and/or cofactors (see e.g. Tables 1A and 1B). Substitutions at these positions may be combined with each other (see also Examples).

Preferably, the mutant 3-3-HBDH from *Rhodobacter sphaeroides* with improved performance relative to the wild-type 3-HBDH comprises an amino acid sequence that is at least 80% identical to the amino acid sequence of SEQ ID NO: 1 (3-HBDH from *Rhodobacter sphaeroides*; wild-type 3-HBDH), has at least one amino acid substitution relative to the wild-type 3-HBDH at a position corresponding to position 250, preferably 250Met, of SEQ ID NO: 1 and has at least one further amino acid substitution at one or more of the position(s) corresponding to position(s) 66, 109 113, 125, 140, 144, 145, 195, 197, 217, 223, 232, 239 and/or 257 of SEQ ID NO: 1, particularly at least position(s) 125, 144 and/or 232 of SEQ ID NO: 1, more particularly at least position(s) 125 and/or 144, of SEQ ID NO: 1.

Particularly suitable examples of substitutions for a mutant 3-HBDH of the present invention are given in the following:
  position 66 of SEQ ID NO: 1 is substituted with Tyr (66Tyr), or Asn (66Asn);
  position 109 of SEQ ID NO: 1 is substituted with Glu (109Glu);
  position 113 of SEQ ID NO: 1 is substituted with Thr (113Thr);
  position 125 of SEQ ID NO: 1 is substituted with Phe (125Phe);
  position 140 of SEQ ID NO: 1 is substituted with Val (140Val);
  position 144 of SEQ ID NO: 1 is substituted with Arg (144Arg);
  position 145 of SEQ ID NO: 1 is substituted with Gly (145Gly);
  position 195 of SEQ ID NO: 1 is substituted with Gln (195Gln) or Leu (195Leu);
  position 197 of SEQ ID NO: 1 is substituted with Ile (197Ile);
  position 217 of SEQ ID NO: 1 is substituted with Val (217Val);
  position 223 of SEQ ID NO: 1 is substituted with Val (223Val);
  position 232 of SEQ ID NO: 1 is substituted with Cys (232Cys), Tyr (232Tyr), or Trp (232Trp), especially 232Cys;
  position 239 of SEQ ID NO: 1 is substituted with Tyr (239Tyr), or Trp (239Trp);
  position 250 of SEQ ID NO: 1 is substituted with Met (250Met); and/or
  position 257 of SEQ ID NO: 1 is substituted with Met (257Met), or Gln (257Gln).

Moreover, the above substitutions may be combined with one or more of the following substitutions:
  position 37 of SEQ ID NO: 1 is substituted with Tyr (37Tyr);
  position 202 of SEQ ID NO: 1 is substituted with Gly (202Gly), and/or
  position 230 of SEQ ID NO: 1 is substituted with Leu (230Leu),
wherein these are preferably combined with 250Met.

In a particularly preferred embodiment of the present invention,
  a) the mutant 3-HBDH has at least the mutations 125Phe, 144Arg, 232Cys, and/or 250Met, particularly 125Phe, 144Arg, and/or 250Met, more particularly 250Met corresponding to positions of SEQ ID NO:1; or
  b) the mutant 3-HBDH has the mutations
    125Phe;
    144Arg;
    232Cys;
    250Met;
    230Leu and 250Met;
    37Tyr and 250Met;
    37Tyr, 230Leu and 250Met;
    202Gly, 230Leu and 250Met;
    37Tyr, 145Gly, 230Leu and 250Met; and/or
    37Tyr, 195Gln, 230Leu and 250Met
    corresponding to positions of SEQ ID NO:1; or
  c) the mutant 3-HBDH has only the mutations
    125Phe;
    144Arg;
    232Cys;
    250Met;
    230Leu and 250Met;
    37Tyr and 250Met;
    37Tyr, 230Leu and 250Met;
    202Gly, 230Leu and 250Met;
    37Tyr, 145Gly, 230Leu and 250Met; or
    37Tyr, 195Gln, 230Leu and 250Met
    corresponding to positions of SEQ ID NO:1.

In a even more particularly preferred embodiment of the present invention, the mutant comprises an amino acid sequence that is at least 80% identical to the amino acid sequence of SEQ ID NO: 1 (3-HBDH from *Rhodobacter sphaeroides*; wild-type 3-HBDH), has at least one amino acid substitution relative to the wild-type 3-HBDH at a position corresponding to position 250, preferably 250Met, of SEQ ID NO: 1 and
  a) has at least the mutations 125Phe, 144Arg, and/or 232Cys, particularly 125Phe and/or 144Arg, corresponding to positions of SEQ ID NO:1; or
  b) the mutant 3-HBDH has the mutations
    125Phe;
    144Arg;
    232Cys;
    250Met;
    230Leu and 250Met;
    37Tyr and 250Met;
    37Tyr, 230Leu and 250Met;
    202Gly, 230Leu and 250Met;
    37Tyr, 145Gly, 230Leu and 250Met; and/or
    37Tyr, 195Gln, 230Leu and 250Met
    corresponding to positions of SEQ ID NO:1; or
  c) the mutant 3-HBDH has only the mutations
    250Met;
    230Leu and 250Met;
    37Tyr and 250Met;
    37Tyr, 230Leu and 250Met;
    202Gly, 230Leu and 250Met;
    37Tyr, 145Gly, 230Leu and 250Met; or
    37Tyr, 195Gln, 230Leu and 250Met
    corresponding to positions of SEQ ID NO:1.

In a preferred embodiment of the present invention, the mutant 3-HBDH comprises or consists of an amino acid sequence that is at least 85%, 90%, 95%, 96%, 97%, 98%, or 99% identical to the amino acid sequence of any of SEQ ID NO: 1 to 11, particularly wherein the mutant 3-HBDH comprises or consists of the sequence selected from the group consisting of SEQ ID NOs: 2 to 11.

As detailed above, the sequence of SEQ ID NO: 1 relates to the wild-type 3-HBDH. The sequences of SEQ ID NO: 2 to 11 are the sequences of preferred mutants. The sequences of SEQ ID NO: 5 to 11 are the sequences of highly preferred mutants. The sequences of the mutants and the substitutions effected are shown in the section "Sequences". Sequence identity may be determined as described above.

In a preferred embodiment of the present invention, improved performance relative to the wild-type 3-HBDH is
  increased stability, especially thermal stability, relative to the wild-type 3-HBDH; and/or
  increased substrate affinity, especially for 3-hydroxybutyrate, relative to the wild-type 3-HBDH; and/or
  increased cofactor affinity, especially for NAD or a derivative thereof, particularly wherein the derivate is carba-NAD, relative to the wild-type 3-HBDH.

The term "increased stability, especially thermal stability, relative to the wild-type 3-HBDH" means that the mutant 3-HBDH is less prone to loss of (enzyme) activity at a certain condition, especially at elevated temperatures. Stabilization of enzymes including avoidance of denaturation mechanisms in order to maintain their full potential as catalysts is an important goal in biotechnology. Enzyme stabilization has notable importance due to increasing number of enzyme applications. The increase in stability allows for sustained usability (e.g. longer storage, usability for a longer time etc). Increased stability of the mutant relative to the wild-type can be determined by comparing the remaining activity of both enzymes (wild-type and mutant), e.g. after storage or exposure to a particular condition (e.g. elevated temperature, drying, buffer, or salt) (absolute remaining activity). Alternatively, the stability is improved compared to the wild-type, if the mutant, e.g., has a higher relative remaining activity in converting 3-HB into acetoacetate. Relative remaining activity may be determined by comparing the remaining or residual acidity after storage at given conditions (e.g. storage time, temperature) to the initial activity before storage. Alternatively, stability is improved, if the mutant, e.g., has a higher remaining activity in converting 3-HB into acetoacetate than the wild type enzyme. Relative remaining activity may be determined by comparing the remaining or residual activities of wild type and mutant enzyme after storage at given conditions (e.g. storage time, temperature).

The term enzyme activity and its determination are well-known to the person skilled in the art. Enzyme activity is generally defined as conversion of amount of substrate per time. The SI unit for enzyme activity is katal (1 katal=1 mol $s^{-1}$). A more practical and commonly used value is enzyme unit (U)=1 µmol $min^{-1}$. 1 U corresponds to 16.67 nanokatals and is defined as the amount of the enzyme that catalyzes the conversion of 1 micro mole of substrate per minute. The specific activity of an enzyme is the activity of an enzyme per milligram of total protein (expressed in µmol $min^{-1}$ $mg^{-1}$).

The enzyme activity may be determined in an assay measuring either the consumption of substrate or cofactor or the formation of product over time. A large number of different methods of measuring the concentrations of substrates and products exist and many enzymes can be assayed in several different ways as known to the person skilled in the art. In the present invention, the 3-HBDH in question is, e.g., incubated with 3-hydroxybutyrate and cofactor (e.g. NAD or derivative thereof such as carba-NAD) and the conversion of the cofactor (NAD to NADH or carba-NAD to carba-NADH) is monitored. Monitoring can, e.g., be done by measuring light absorbance at 340 nm. The obtained change of absorption per minute (dE/min) represents the enzymatic activity. For details see Example 2.

In a preferred embodiment of the present invention, increased stability of the mutant 3-HBDH relative to the respective 3-HBDH without mutation may be expressed as increase in half-life of the mutant ($t_{1/2}$(mutant)) relative to the half-life of to the respective wild-type 3HBDH ($t_{1/2}$(wild-type)). The half-life ($t_{1/2}$) of the enzyme indicates the amount of time in which 50% of the original activity (activity at t=0) is lost and after which the remaining activity amounts to 50%. Accordingly, an increased stability results in an increased half-life of the mutant relative to the respective wild-type. Increase in stability may be determined as $t_{1/2}$(mutant)/$t_{1/2}$(wild-type). Percental increase in half-life may be determined as $[t_{1/2}$(mutant)/$t_{1/2}$(wild-type)$-1]*100$.

In a highly preferred embodiment of the present invention, increased stability of the mutant 3-HBDH relative to the respective 3-HBDH without mutation may be determined and expressed as remaining activity after a stress incubation (e.g. 30 min at e.g. 64° C. or any other condition given in the Examples) in relation to the initial activity before stress incubation/storage (see Examples). For this, the enzymatic reaction may be monitored (e.g. at room temperature at 340 nm for 5 minutes) and the change in absorption per time (e.g. dE/min) may be calculated for each sample. The values obtained for stressed samples may be compared to the respective un-stressed sample (value set to 100% activity) and calculated in percent activity ((dE/min (stressed sample)/dE/min (unstressed sample)*100). Accordingly, a mutant's value higher than the value obtained with wild-type enzyme represents an improvement in thermal stability. The stability is increased, if [% remaining activity of the mutant]–[% remaining activity of the wild-type]>0. Alternatively, the remaining activity of the mutant may be also expressed as activity in percent and may be calculated as follows: [% remaining activity of the mutant]/[% remaining activity of the wild-type]*100%. The stability of the mutant relative to the wild-type is increased if the resulting value is >100%. A particular suitable test for determining stability is described in detail in Example 2. In accordance with this, the stability may be expressed as remaining activity and calculated as [dE/min (stressed sample)]/[dE/min (not stressed sample)]*100. Further details are given in Example 2. A value obtained with a mutant higher than the value obtained with wild-type enzyme represents an increased stability of the mutant.

Preferably, stability is increased by at least 10%, 20%, 30% or 40%, preferably at least 50%, 75% or 100%, still more preferably at least 125%, 150%, 175% or 200%, especially 250% and most preferably 300%.

Moreover, there are commercial advantages in carrying out enzymatic reactions at higher temperatures. Accordingly, thermal stability of the mutant is preferably increased. This means that resistance of the mutant relative to the wild-type to increased temperatures is higher. Increase in thermal stability may be particularly determined as shown in the Examples, e.g. in Examples 2 and 3. In general, the mutant and the wild-type enzyme may be preincubated at an increased temperature (e.g. above 50° C. such as 54° C. or 64° C.) for a defined time (such as 10 min or 30 min), after which the remaining activity in converting 3-HB into acetoacetate of the mutant is compared to the remaining activity of the wild-type enzyme. If the remaining activity of the mutant is higher than that of the wild-type, the mutant has an increased thermal stability.

A suitable method for the determination of increased thermal stability is detailed in the Examples. Exemplary conditions for stress conditions may be preincubation at 50-90° C., in particular at 50-64° C. (e.g., 50° C. or 54° C. or 64° C.) for 30 min and testing afterwards with 62.22 mM 3-hydroxybutyrate; 4.15 mM cNAD; 0.1% Triton X-100; 200 mM Hepes pH 9.0 or 150 mM 3-hydroxybutyrate; 5 mM cNAD; 0.1% Triton X-100; 70 mM Mops pH 7.5.

The term "increased substrate affinity, especially for 3-hydroxybutyrate, relative to the wild-type 3-HBDH" means that the affinity of the mutant for the substrate 3-hydroxybutyric acid/3-hydroxybutyrate/3-hydroxybutanoate (3-HB) which is converted into acetoacetate is increased. For the determination, the enzymatic reaction may be monitored (e.g. at room temperature at 340 nm for 5 minutes) and the dE/min may be calculated for each sample. The affinity of the mutant is increased compared to the wild-type, if the mutant, e.g., has a higher absolute or relative affinity for the substrate, particularly 3-HB. Affinity of the mutant compared to the wild-type can be determined by comparing the absolute affinities of both enzymes (wild-type and mutant)

(absolute comparison) and may be calculated in percent activity ((dE/min (mutant)/dE (wild-type))*100) (%). Alternatively, the affinity of the mutant compared to the wild-type can be determined by comparing the relative affinities of both enzymes (wild-type and mutant) (relative comparison). Relative affinity of wild-type or mutant may be determined by setting the affinity at subsaturation substrate concentration in relation to the affinity at saturation substrate concentration. As detailed in the Examples 2 and 3, affinity to 3-hydroxybutyrate may be determined in an activity assay with reduced amount of substrate (i.e. at subsaturation concentration), e.g. with 1.94 mM 3-hydroxybutyrate (further exemplary conditions: 4.15 mM cNAD; 0.1% Triton X-100; 200 mM Hepes pH 9.0). A particular suitable test for determining affinity is described in detail in Example 2. In accordance with this, the affinity may be expressed as relative activity and calculated as [dE/min (subsaturation substrate concentration)]/[dE/min (saturation substrate concentration)]*100. Further details are given in Example 2. A value obtained with a mutant higher than the value obtained with wild-type enzyme represents an increase in affinity for the mutant.

An increased affinity correlates with a lower Km value. The Michaelis constant Km is the substrate concentration at which an enzyme reaction rate is at half-maximum and is an inverse measure of the substrate's affinity for the enzyme.

The term "increased cofactor affinity, especially for NAD or a derivative thereof, particularly wherein the derivate is carba-NAD, relative to the wild-type 3-HBDH" means that the affinity of the mutant for the cofactor (NAD or a derivate thereof, especially carba-NAD) needed to convert 3-HB into acetoacetate is increased. As detailed in the Examples 2 and 3, affinity to the cofactor may be determined in an activity assay with reduced amount of cofactor (i.e. below saturation), e.g. with 0.032 mM cNAD (further exemplary conditions: 62.22 mM 3-hydroxybutyrate; 0.1% Triton X-100; 200 mM Hepes pH 9.0) or 0.5 mM cNAD. The above details given with respect to substrate affinity are analogously applicable to the cofactor affinity. A particular suitable test for determining affinity is described in detail in Example 2.

Particularly, the mutant 3-HBDH of the present invention is characterized in that the mutant 3-HBDH has an at least 2-fold increased stability relative to the wild-type 3-HBDH, preferably an at least 3-fold increased stability, preferably an at least 4-fold increased stability, more preferably an at least 5-fold increased stability; and/or characterized in that the mutant 3-HBDH has an increased substrate and/or cofactor affinity relative to the wild-type 3-HBDH, particularly an increased affinity for (i) 3-hydroxybutyrate and/or (ii) nicotinamide adenine dinucleotide (NAD) or a functionally active derivative thereof and/or particularly wherein the substrate and/or cofactor affinity is increased by at least 5%, more particularly at least 10%, still more particularly by at least 15% or 20%.

In another aspect, the present invention relates to a nucleic acid encoding the mutant 3-HBDH of the present invention as described above.

The term "nucleic acid" as used herein generally relates to any nucleotide molecule which encodes the mutant 3-HBDH of the invention and which may be of variable length. Examples of a nucleic acid of the invention include, but are not limited to, plasmids, vectors, or any kind of DNA and/or RNA fragment(s) which can be isolated by standard molecular biology procedures, including, e.g. ion-exchange chromatography. A nucleic acid of the invention may be used for transfection or transduction of a particular cell or organism.

Nucleic acid molecule of the present invention may be in the form of RNA, such as mRNA or cRNA, or in the form of DNA, including, for instance, cDNA and genomic DNA e.g. obtained by cloning or produced by chemical synthetic techniques or by a combination thereof. The DNA may be triple-stranded, double-stranded or single-stranded. Single-stranded DNA may be the coding strand, also known as the sense strand, or it may be the non-coding strand, also referred to as the anti-sense strand. Nucleic acid molecule as used herein also refers to, among other, single- and double-stranded DNA, DNA that is a mixture of single- and double-stranded RNA, and RNA that is a mixture of single- and double-stranded regions, hybrid molecules comprising DNA and RNA that may be single-stranded or, more typically, double-stranded, or triple-stranded, or a mixture of single- and double-stranded regions. In addition, nucleic acid molecule as used herein refers to triple-stranded regions comprising RNA or DNA or both RNA and DNA.

Additionally, the nucleic acid may contain one or more modified bases. Such nucleic acids may also contain modifications e.g. in the ribose-phosphate backbone to increase stability and half life of such molecules in physiological environments. Thus, DNAs or RNAs with backbones modified for stability or for other reasons are "nucleic acid molecule" as that feature is intended herein.

Moreover, DNAs or RNAs comprising unusual bases, such as inosine, or modified bases, such as tritylated bases, to name just two examples, are nucleic acid molecule within the context of the present invention. It will be appreciated that a great variety of modifications have been made to DNA and RNA that serve many useful purposes known to those of skill in the art. The term nucleic acid molecule as it is employed herein embraces such chemically, enzymatically or metabolically modified forms of nucleic acid molecule, as well as the chemical forms of DNA and RNA characteristic of viruses and cells, including simple and complex cells, inter alia.

Furthermore, the nucleic acid molecule encoding the mutant 3-HBDH of the invention can be functionally linked, using standard techniques such as standard cloning techniques, to any desired sequence, such as a regulatory sequence, leader sequence, heterologous marker sequence or a heterologous coding sequence to create a fusion protein.

The nucleic acid of the invention may be originally formed in vitro or in a cell in culture, in general, by the manipulation of nucleic acids by endonucleases and/or exonucleases and/or polymerases and/or ligases and/or recombinases or other methods known to the skilled practitioner to produce the nucleic acids.

The nucleic acid of the invention may be comprised in an expression vector, wherein the nucleic acid is operably linked to a promoter sequence capable of promoting the expression of the nucleic acid in a host cell.

As used herein, the term "expression vector" generally refers to any kind of nucleic acid molecule that can be used to express a protein of interest in a cell (see also above details on the nucleic acids of the present invention). In particular, the expression vector of the invention can be any plasmid or vector known to the person skilled in the art which is suitable for expressing a protein in a particular host cell including, but not limited to, mammalian cells, bacterial cell, and yeast cells. An expression construct of the present invention may also be a nucleic acid which encodes a 3-HBDH of the invention, and which is used for subsequent cloning into a respective vector to ensure expression. Plasmids and vectors for protein expression are well known in the art, and can be commercially purchased from diverse suppliers including, e.g., Promega (Madison, Wis., USA), Qiagen (Hilden, Germany), Invitrogen (Carlsbad, Calif., USA), or MoBiTec (Germany). Methods of protein expression are well known to the person skilled in the art and are, e.g., described in Sambrook et al., 2000 (Molecular Cloning: A laboratory manual, Third Edition).

The vector may additionally include nucleic acid sequences that permit it to replicate in the host cell, such as an origin of replication, one or more therapeutic genes and/or selectable marker genes and other genetic elements known in the art such as regulatory elements directing transcription, translation and/or secretion of the encoded protein. The vector may be used to transduce, transform or infect a cell, thereby causing the cell to express nucleic acids and/or proteins other than those native to the cell. The vector optionally includes materials to aid in achieving entry of the nucleic acid into the cell, such as a viral particle, liposome, protein coating or the like. Numerous types of appropriate expression vectors are known in the art for protein expression, by standard molecular biology techniques. Such vectors are selected from among conventional vector types including insects, e.g., baculovirus expression, or yeast, fungal, bacterial or viral expression systems. Other appropriate expression vectors, of which numerous types are known in the art, can also be used for this purpose. Methods for obtaining such expression vectors are well-known (see, e.g. Sambrook et al, supra).

As detailed above, the nucleic acid which encodes a mutant 3-HBDH of the invention is operably linked to sequence which is suitable for driving the expression of a protein in a host cell, in order to ensure expression of the protein. However, it is encompassed within the present invention that the claimed expression construct may represent an intermediate product, which is subsequently cloned into a suitable expression vector to ensure expression of the protein. The expression vector of the present invention may further comprise all kind of nucleic acid sequences, including, but not limited to, polyadenylation signals, splice donor and splice acceptor signals, intervening sequences, transcriptional enhancer sequences, translational enhancer sequences, drug resistance gene(s) or alike. Optionally, the drug resistance gene may be operably linked to an internal ribosome entry site (IRES), which might be either cell cycle-specific or cell cycle-independent.

The term "operably linked" as used herein generally means that the gene elements are arranged as such that they function in concert for their intended purposes, e.g. in that transcription is initiated by the promoter and proceeds through the DNA sequence encoding the protein of the present invention. That is, RNA polymerase transcribes the sequence encoding the fusion protein into mRNA, which in then spliced and translated into a protein.

The term "promoter sequence" as used in the context of the present invention generally refers to any kind of regulatory DNA sequence operably linked to a downstream coding sequence, wherein said promoter is capable of binding RNA polymerase and initiating transcription of the encoded open reading frame in a cell, thereby driving the expression of said downstream coding sequence. The promoter sequence of the present invention can be any kind of promoter sequence known to the person skilled in the art, including, but not limited to, constitutive promoters, inducible promoters, cell cycle-specific promoters, and cell type-specific promoters.

Another aspect of the present invention relates to a cell comprising the mutant 3-HBDH of the present invention or the nucleic acid of the present invention. In one embodiment of the present invention, a cell comprising the mutant is used in the context of the present invention. The cell is preferably a host cell. A "host cell" of the present invention can be any kind of organism suitable for application in recombinant DNA technology, and includes, but is not limited to, all sorts of bacterial and yeast strain which are suitable for expressing one or more recombinant protein(s). Examples of host cells include, for example, various *Bacillus subtilis* or *E. coli* strains. A variety of *E. coli* bacterial host cells are known to a person skilled in the art and include, but are not limited to, strains such as DH5-alpha, HB101, MV1190, JM109, JM101, or XL-1 blue which can be commercially purchased from diverse suppliers including, e.g., Stratagene (CA, USA), Promega (WI, USA) or Qiagen (Hilden, Germany). A particularly suitable host cell is also described in the Examples, namely *E. coli* XL-1 Blue cells. *Bacillus subtilis* strains which can be used as a host cell include, e.g., 1012 wild type: leuA8 metB5 trpC2 hsdRM1 and 168 Marburg: trpC2 (Trp−), which are, e.g., commercially available from MoBiTec (Germany).

The cultivation of host cells according to the invention is a routine procedure known to the skilled person. That is, a nucleic acid encoding a mutant 3-HBDH of the invention can be introduced into a suitable host cell(s) to produce the respective protein by recombinant means. These host cells can by any kind of suitable cells, preferably bacterial cells such as *E. coli*, which can be easily cultivated. At a first step, this approach may include the cloning of the respective gene into a suitable plasmid vector. Plasmid vectors are widely used for gene cloning, and can be easily introduced, i.e. transformed, into bacterial cells which have been made competent. After the protein has been expressed in the respective host cell, the cells can be broken by means of either chemical or mechanical cell lysis are well known to the person skilled in the art, and include, but are not limited to, e.g. hypotonic salt treatment, detergent treatment, homogenization, or ultrasonification.

In another aspect the present invention relates to a method of determining the amount or concentration of 3-hydroxy-butyrate in a sample, the method comprising a) contacting the sample with the mutant 3-HBDH of the present invention under conditions conducive to the activity of the 3-HBDH;
b) reacting 3-hydroxybutyrate with nicotinamide adenine dinucleotide (NAD) or a functionally active derivative thereof; and
c) determining the change in the redox state of NAD or the derivative thereof, thereby determining the amount or concentration of 3-hydroxybutyrate in the sample.

The above method is based on the fact that 3-HBDH may be used to catalyze the conversion of 3-HB to acetoacetate according to the following scheme:

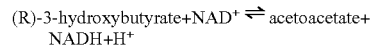

In a first step of the method of the present invention a sample is contacted with the 3-HBDH of the present invention. The contacting of the sample with the mutant 3-HBDH can be direct (e.g. in liquid assays) or indirect (e.g. in sensor systems in which only a fraction of the sample (containing the analyte) is contacting the 3-HBDH).

It is evident that the contacting should be carried out under conditions conducive to the activity of the 3-HBDH, i.e. allowing the enzyme to convert 3-HB to acetoacetate. Incubation step can vary from about 5 seconds to several hours, preferably from about 10 seconds to about 10 minutes. However, the incubation time will depend upon the assay format, volume of solution, concentrations and the like. Usually the assay will be carried out at ambient temperature or a temperature required for other test formats carried out concomitantly (e.g. 25° C. to 38° C.; such as 30° C. or 37° C.), although it can be conducted over a range of temperatures, such as 10° C. to 40° C.

Optionally, the enzyme can be fixed to or immobilized into a support layer prior to the contacting with the sample to facilitate the assay. Examples of support layers include glass or plastic in the form of, for example, a microtiter plate, a glass microscope slide or cover slip, a stick, a bead, or a microbead, membranes (e.g. used in test strips) and layers of biosensors.

The sample may be any sample suspected of containing 3-HB, particularly a sample from a subject. The term "sample from a subject" includes all biological fluids, excretions and tissues isolated from any given subject, particularly a human. In the context of the present invention such samples include, but are not limited to, blood, blood serum, blood plasma, nipple aspirate, urine, semen, seminal fluid, seminal plasma, prostatic fluid, excreta, tears, saliva, sweat, biopsy, ascites, cerebrospinal fluid, milk, lymph, bronchial and other lavage samples, or tissue extract samples. Preferably, the subject is an animal (including human), more preferably a mammal, still more preferably a human. Preferably, the sample is a body fluid, particularly a blood sample or a urine sample.

Typically, blood samples are preferred test samples for use in the context of the present invention. For this, blood may be drawn from a vein, usually from the inside of the elbow or the back of the hand or a fingertip. Particularly, in infants or young children, a sharp tool called a lancet may be used to puncture the skin and make it bleed. The blood may be collected e.g. into a pipette or cannula, or onto a slide or test strip.

After the contacting and the conversion of 3-HB, if present, the change in the redox state of NAD or derivate mediated by the 3-HBDH are determined, thereby determining 3-HB in the sample. Evidently, the amount of NADH or derivate thereof produced and the amount of NAD or derivate thereof consumed correlate with the amount of 3-HB present in the sample. Accordingly, the change in the redox state of NAD includes the determination of the amount or concentration of NAD and/or NADH as well as the ratio of the two. The same applies to NAD derivates.

A variety of methods for determining NADH/NAD or derivate thereof are known in the art and any of these can be used.

Exemplary methods for determining NADH/NAD or derivate thereof include electrochemical methods (e.g. as described in U.S. Pat. No. 6,541,216) or optical methods (e.g. by measuring NAD/NADH conversion by light absorbance at e.g. 340 nm or 365 nm or by assays based on a reductase to form luciferin, which is then quantified optically). If electrochemical methods are used, NADH/NAD or derivate thereof can either a) react directly on a measurement electrode or b) NADH/NAD or derivate thereof reacts in a first step with an additional redoxmediator substance which changes its redox state in a defined relation to the redox state of NADH/NAD or derivate thereof and this redoxmediator reacts in a subsequent step on the measurement electrode.

Both NAD and NADP are base-labile molecules the degradation paths of which are described in the literature (see e.g. N.J.Oppenheimer in The Pyridine Nucleotide Coenzymes Academic Press, New York, London 1982, J. Everese, B. Anderson, K. Yon, Editors, chapter 3, pages 56-65). Therefore, derivatives of NADH/NAD have been developed and are commercially available. Some derivates are described in the Pyridine Nucleotide Coenzymes, Academic Press New York, London 1982, Eds. J. Everese, B. Anderson, K. You, Chapter 4, WO 01/94370, WO 98/33936 and U.S. Pat. No. 5,801,006.

Preferably, carba-NAD (cNAD) is used as a derivative of NAD. In carba-NAD the ribose is substituted by a carbacyclic sugar unit. Carba-NAD has the following structure (I):

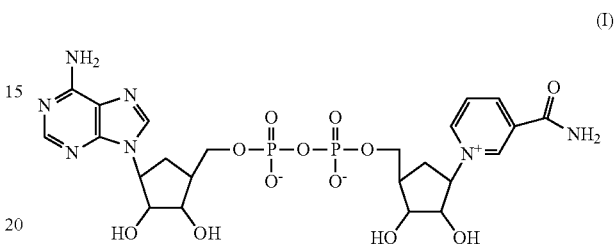

The compound, its production and use are described in detail in WO 2007/012494, WO 2011/012270 and WO2014/195363. The cofactor in the present invention is preferably carba-NAD. In one embodiment of the present invention, the cofactor is a functionally active derivative of NAD as disclosed in formula III of WO 2011/012270 to which it is explicitly referred. In one embodiment of the present invention, NADP is used instead of NAD.

The method of the present invention can be carried out in a so-called liquid or wet test, for example in a cuvette, or as a so-called dry test on an appropriate reagent carrier, the necessary test reagents thereby being present in or on a solid carrier, which is preferably an absorbent or swellable material.

Alternatively or additionally, the 3-HBDH may be part of a sensor, a test strip, a test element, a test strip device or a liquid test.

A sensor is an entity that measures a physical/chemical quantity and converts it into a signal which can be read by an observer or by an instrument. In the present invention, the 3-HBDH may be part of a sensor. The sensor converts 3-HB and NAD or a derivate thereof into acetoacetate and NADH or a derivate thereof, which is further converted into a signal such as a change in colour or a value displayed e.g. on a display or monitor.

In one embodiment, the sensor may comprise 3-HBDH and an amperometric device to determine 3-HB of a sample. Also, a microdialysis system coupled with an electrochemical flow cell could be used for continuous monitoring of 3-HB in a sample or subject. The working electrode of the flow cell could be prepared with the 3-HBDH immobilized in a redox polymer film on the electrode surface. Coupling an electrochemical 3-HB sensor directly with microdialysis eliminates the need to transfer sample aliquots to a liquid chromatography system with a post-column oxidase enzyme reactor. 3-HB in the dialysate from the microdialysis probe can be selectively detected at the enzyme electrode without any significant interference from other oxidizable species. Furthermore, enzyme-coupled biosensors have been described in the art. In accordance with this, 3-HBDH may be coupled to a surface (e.g. by printing a 3-HBDH/graphite mixture onto electroplated graphite pads or by adsorption or immobilization of the mutant 3-HBDH on carbon particles, platinized carbon particles, carbon/manganese dioxide particles, glassy carbon, or mixing it with carbon paste electrodes etc.)

A test strip or a test element is an analytic or diagnostic device used to determine presence and/or quantity of a target substance within a sample. A standard test strip may comprise one or more different reaction zones or pads comprising reagents which react (e.g. change colour) when contacted with a sample. Test strips are known in many embodiments, for example from U.S. Pat. No. 6,541,216, EP 262445 and U.S. Pat. No. 4,816,224. It is commonly known that one or more reagents (e.g. enzymes) needed for carrying out the determination methods are present on or in solid carrier layers. As carrier layers, there are especially preferred absorbent and/or swellable materials which are wetted by the sample liquid to be analyzed. Examples include gelatine, cellulose and synthetic fiber fleece layers.

The 3-HBDH of the present invention may also be part of a liquid test. A liquid test is a test wherein test components react in a liquid medium. Usually in the field of laboratory analytics, the liquid reagents are on water basis, e.g. a buffered salt solution in order to provide the activity of enzyme(s) involved. The liquid is usually adapted to the specific intended use. For carrying out a liquid test, all test components are solved in a liquid and combined (or vice versa). Typical containments for carrying out such tests include vials, multi wells plates, cuvettes, vessels, reagent cups, tubes etc.

In one embodiment of the present invention, the 3-HBDH of the present invention may be immobilized. Typical methods of immobilization include covalent binding e.g. to a membrane, encapsulation in a polymer, cross-linking to a supporting matrix or immobilization in a sol-gel matrix (e.g. glasses such as silicate glasses) or adsorption on porous substrates. Suitable methods for immobilizing enzymes are known in the art (see e.g. Lillis et al., 2000, Sensors and Actuators B 68: 109-114).

In a preferred embodiment of the present invention, the method further comprises determining the amount or concentration of glucose. In another embodiment of the present invention the method comprises determining the amount or concentration of acetone and/or acetoacetate; and/or determining the amount or concentration of glucose. The determination of these compounds is of particular relevance in the diagnosis of the above diseases and medical condition. Methods for determining these compounds are well-known in the art. Additionally, systems and methods for multiple analyte analysis are known from WO 2014/068024.

Accordingly and preferably, the method of the present invention is further characterized in that
a) wherein the determining of the change in the redox state of NAD or the derivate thereof includes the determination of the concentration of (i) NAD or the derivate thereof and/or (ii) NADH or the derivate thereof; and/or
b) wherein the determining the change in the redox state of NAD or the derivative thereof is electrochemically or optically; and/or
c) wherein the method further comprises determining the amount or concentration of acetoacetate and/or acetone; and/or
d) wherein the method further comprises determining the amount or concentration of glucose; and/or
e) wherein the derivative of NAD is carba-NAD; and/or
f) wherein the mutant 3-HBDH is part of a sensor, a test strip, a test element, a test strip device or a liquid test; and/or
g) wherein the sample is a body fluid, particularly a blood sample or a urine sample.

In still another aspect, the present invention relates to the use of the mutant 3-HBDH of the present invention for determining the amount or concentration of 3-hydroxybutyrate in a sample.

With respect to the use of the present invention it is referred to the terms, examples and specific embodiments used in the context of the other aspects of the present disclosure, which are also applicable to this aspect. Particularly, the mutant 3-HBDH according to the present invention may be used as detailed with respect to the methods of the present invention.

Yet, in another aspect, the present invention relates to a device for determining the amount or concentration of 3-hydroxybutyrate in a sample comprising the mutant 3-HBDH of the present invention and optionally a further component required for said determining.

With respect to the device of the present invention it is referred to the terms, examples and specific embodiments used in the context of the other aspects of the present disclosure, which are also applicable to this aspect. Particularly, the mutant 3-HBDH according to the present invention may be employed as detailed above.

The 3-HBDH of the present invention may be part of a device for determining 3-HB in a sample. The device may be any device suitable for this purpose. The device may be a machine or tool which can be used for determining 3-HB. Preferably, the device is a sensor, preferably an electrochemical sensor, or a test strip. Exemplary devices are described above and in the following:

The device may be a sensor, e.g. a biosensor, which is an analytical device for the detection of an analyte that combines a biological component (here the 3-HBDH according to the present invention) with a detector component, particularly a physicochemical detector component.

Biosensors are particularly useful to determine the concentration of various analytes (including 3-HB) from biological samples, particularly from blood. Exemplary biosensors based on an electrochemical test strip format are described in U.S. Pat. Nos. 5,413,690; 5,762,770 and 5,997,817.

In the (bio)sensor of the present invention, 3-HB converted into acetoacetate in the presence of the 3-HBDH and NAD or derivative and the change in the redox state of NAD or derivative may be monitored by the transducer or detector element.

Particularly, 3-HB sensors have been combined with other sensors, e.g. for determining glucose, acetone, acetoacetate, cholesterol, triglycerides, urea, blood gases or electrolytes etc. Evidently, the mutant 3-HBDH of the present invention could also be used in these multi-analyte devices.

As detailed above, the sensor is preferably an electrochemical or optical sensor. An electrochemical sensor is based on the translation of a chemical signal (here presence of 3-HB) into an electrical signal (e.g. current). A suitable electrode can measure the 3-HB-mediated production of NADH or derivative thereof as an electrical signal.

A suitable optical sensor can measure the 3-HBDH-mediated change in the redox state of NAD or derivate thereof. The signal may be the NAD/NADH-mediated absorbance/emission of light.

The device of the present invention may comprise—in addition to the 3-HBDH of the present invention—one or more further component(s), such as other reagents, required for or helpful in said determining. The components may be any of these described in the context of the methods and devices of the present invention. Additionally, this may include an instruction manual, a lancet device, a capillary pipette, a further enzyme, a substrate and/or a control solution etc.

Preferably, the device of the present invention is characterized in that the device is or comprises a sensor, preferably an electrochemical sensor or an optical sensor, or a test strip, particularly a test strip and/or allows for determining the amount or concentration of glucose in the sample. With respect to the device of the present invention it is also referred to the terms, examples and specific embodiments described above.

Unless defined otherwise, all technical and scientific terms and any acronyms used herein have the same meanings as commonly understood by one of ordinary skill in the art in the field of the invention. Definitions of common terms in molecular biology can be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

The invention is not limited to the particular methodology, protocols, and reagents described herein because they may vary. Although any methods and materials similar or equivalent to those described herein can be used in the practice of the present invention, the preferred methods, and materials are described herein. Further, the terminology used herein is for the purpose of describing particular embodiments only and is not intended to limit the scope of the present invention.

As used herein and in the appended claims, the singular forms "a", "an", and "the" include plural reference unless the context clearly dictates otherwise. Similarly, the words "comprise", "contain" and "encompass" are to be interpreted inclusively rather than exclusively. Similarly, the word "or" is intended to include "and" unless the context clearly indicates otherwise. The term "plurality" refers to two or more.

The following Examples are intended to illustrate various embodiments of the invention. As such, the specific modifications discussed are not to be construed as limitations on the scope of the invention. It will be apparent to the person skilled in the art that various equivalents, changes, and modifications may be made without departing from the scope of the invention, and it is thus to be understood that such equivalent embodiments are to be included herein.

EXAMPLES

Example 1 Establishing a Library of 3-HBDH Mutants

The gene for 3-hydroxybutyrate dehydrogenase (3-HBDH) from *Rhodobacter sphaeroides* (Database UniProtKB-D0VWQ0) was synthesized, cloned in vector pKKt5 and transformed in *E. coli* strain XL-1 Blue by common methods of molecular biology.

Saturation mutagenesis was applied on many amino acid positions of the enzyme. Mutagenesis was achieved by applying randomly synthesized primers with QuikChange Site-Directed Mutagenesis Kit (Agilent Technologies Cat. 200518).

The 5'- and the 3'-primer used for mutagenesis were complementary to each other and contained NNN (randomly synthesized nucleotides) for the amino acid exchange in a central position. This randomly created codon was flanked by 12 to 16 nucleotides at each end. The sequences of these nucleotides were identical to the cDNA-strand or to the complementary cDNA-strand flanking the codon for the amino substitution. Mutant library was created by transformation of mutated genes in *E. coli* strain XI-Blue and cultivation on agar plates over night at 37° C.

Example 2 Determination of Properties of 3-HBDH Mutants from First Round of Mutagenesis (Mutants with Single Amino Acid Substitutions)

A library of 3-HBDH mutants produced as described in Example 1 was screened for the following enzymatic properties:
Thermal stability
Affinity for 3-hydroxybutyrate
Affinity for c-NAD (carba-NAD=artificial cofactor cf. US20120130062A1)

Mutant colonies on agar plates described above were picked in microtiter plates (mtp) containing 200 µl LB-Ampicillin-media/hole and incubated at 37° C. over night. These plates were referred to as master plates. For each amino acid position two master plates were picked to assure that every possible exchange is included.

From each master plate, 40 µl sample/cavity was transferred to a mtp containing 200 µl 0.1% Triton X-100; 500 mM NaCl; 200 mM Hepes pH 9.0; 2% B-Per/cavity (B-PER=Bacterial Protein Extraction Reagent Pierce No. 78248) and incubated for cell disruption at 40° C. for 30 minutes. This plate was referred to as working plate.

From the working plate 4×20 µl sample/cavity was transferred to four empty mtps. One of these was tested with 62.22 mM 3-hydroxybutyrate; 4.15 mM cNAD; 0.1% Triton X-100; 200 mM Hepes pH 9.0 at room temperature and referred to as reference measurement. The other mtps were tested under different conditions and the obtained values compared to the reference plate in percent.

Following parameters were measured:
Thermal stability: Mtp was incubated for 30 min. at 50° C. (unless indicated otherwise) and tested afterwards with 62.22 mM 3-hydroxybutyrate; 4.15 mM cNAD; 0.1% Triton X-100; 200 mM Hepes pH 9.0
Affinity to 3-hydroxybutyrate: Activity assay with reduced amount of substrate (i.e. below substrate saturation). Measurement with 1.94 mM 3-hydroxybutyrate; 4.15 mM cNAD; 0.1% Triton X-100; 200 mM Hepes pH 9.0
Affinity to cNAD: Activity assay with reduced amount of cofactor (i.e. below saturation). Measurement with 62.22 mM 3-hydroxybutyrate; 0.032 mM cNAD; 0.1% Triton X-100; 200 mM Hepes pH 9.0

The enzymatic reaction was monitored at room temperature at 340 nm for 5 minutes and the dE/min calculated for each cavity in each working plate. The value from the reference measurement was set to 100% activity. The values obtained with the other three plates (thermal stability, affinity to 3-hydroxybutyrate or cNAD) were compared to the reference and calculated in percent activity ((dE/min Parameter/dE/min Reference)*100). Each master plate contained beside the mutants wild-type enzyme as control to better estimate improvements or deteriorations of the properties.

Thermal stability expressed as remaining activity was calculated as follows:

$$\left(\frac{dE/\text{min stressed sample}}{dE/\text{min not stressed sample}}\right)*100=$$

$$\text{remaining activity in percent}$$

A value obtained with a mutant higher than the value obtained with wild-type enzyme represents an increase in thermal stability for the mutant.

Substrate affinity expressed as activity ratio was calculated as follows:

$$\left(\frac{dE/\text{min obtained with less substrate}}{dE/\text{min obtained with substrate in saturation}}\right)*100=\text{activity in percent}$$

A mutant with higher substrate affinity will show higher activity when reacted with less substrate (below substrate saturation) than a mutant with lower substrate affinity. A value obtained with a mutant higher than the value obtained with wild-type enzyme represents an increase in substrate affinity for the mutant.

Cofactor affinity expressed as activity ratio was calculated accordingly:

$$\left(\frac{dE/\text{min obtained with less cofactor}}{dE/\text{min obtained with cofactor in saturation}}\right)*100=\text{activity in percent}$$

Data below 0.001 dE/min were set to zero, resulting in "zero" values.

The results relative to wild type enzyme are summarized in Tables 1A and 1B.

In a first round of saturation mutagenesis the following mutants were found:

TABLE 1A

Thermal stability and affinity of various single mutants relative to the wild-type 3-HBDH referred to as WT

| Clone | Affinity for 3-HB | Affinity for cNAD | Thermal Stability |
|---|---|---|---|
| WT + D2G | + | o | o |
| WT + D2S | + | o | + |
| WT + N4T | + | nt | o |
| WT + N4C | + | nt | o |
| WT + T11P | + | + | + |
| WT + N14T | + | nt | o |
| WT + E23N | + | o | − |
| WT + F37Y | + | nt | + |
| WT + E42C | o | o | + |
| WT + S57N | + | nt | o |
| WT + S57C | + | nt | + |
| WT + S57Y | + | nt | o |
| WT + S57P | + | nt | + |
| WT + A62P | + | o | o |
| WT + A62R | ++ | o | + |
| WT + S66N | o | o | ++ |
| WT + S66Y | o | o | ++ |
| WT + D67C | o | o | + |
| WT + E69M | + | o | + |
| WT + E76D | o | o | + |
| WT + D87A | − | nt | + |
| WT + Q90T | − | nt | + |
| WT + H92Q | ++ | o | −− |

TABLE 1A-continued

Thermal stability and affinity of various single mutants relative to the wild-type 3-HBDH referred to as WT

| Clone | Affinity for 3-HB | Affinity for cNAD | Thermal Stability |
|---|---|---|---|
| WT + S94A | + | nt | + |
| WT + S95R | ++ | ++ | + |
| WT + E97I | + | + | − |
| WT + E98T | o | o | + |
| WT + A106E | o | o | + |
| WT + A109E | o | o | ++ |
| WT + A109T | o | o | ++ |
| WT + N111I | − | nt | + |
| WT + S113T | o | o | ++ |
| WT + A115Y | − | − | + |
| WT + G125F | + | o | ++ |
| WT + A128K | o | o | + |
| WT + A140V | − | − | ++ |
| WT + T144R | + | o | + |
| WT + T144V | − | o | + |
| WT + A145G | o | o | + |
| WT + P147R | + | + | − |
| WT + P147Q | + | + | − |
| WT + V165T | − | − | + |
| WT + V185I | + | + | − |
| WT + L186K | + | o | − |
| WT + P188E | − | − | + |
| WT + P195Q | − | − | ++ |
| WT + P195L | − | − | ++ |
| WT + D196L | − | − | + |
| WT + Q197I | − | − | ++ |
| WT + A200K | − | nt | + |
| WT + A200L | + | nt | o |
| WT + D202G | + | + | + |
| WT + D202N | + | + | + |
| WT + M203V | + | + | − |
| WT + T207R | + | + | − |
| WT + V208Y | − | nt | ++ |
| WT + V212I | ++ | o | − |
| WT + Q217V | − | − | ++ |
| WT + A223V | − | − | ++ |
| WT + T225P | o | o | + |
| WT + G226K | o | o | + |
| WT + G230C | ++ | nt | − |
| WT + G230L | ++ | nt | o |
| WT + V232C | + | o | ++ |
| WT + V232Y | o | o | ++ |
| WT + V232W | o | o | ++ |
| WT + V232P | + | + | − |
| WT + A239V | + | o | − |
| WT + A239Y | o | o | ++ |
| WT + A239W | o | o | ++ |
| WT + A239P | + | o | − |
| WT + V250I | ++ | nt | + |
| WT + V250M | + | o | ++ |
| WT + L257M | o | o | ++ |
| WT + L257Q | − | − | ++ |
| WT + L257M | o | o | ++ |

(+ = improved; o = similar; − = decreased; nt = not tested)

TABLE 1B

Thermal stability and affinity of various single mutants of 3-HBDH

| Clone | Affinity for* 3-HB | Affinity for* cNAD | Thermal Stability** |
|---|---|---|---|
| WT | 33 | 9 | 16 |
| WT + S66Y | 34 | 10 | 100 |
| WT + S66N | 35 | 8 | 95 |
| WT + A109E | 26 | 5 | 99 |
| WT + S113T | 34 | 11 | 100 |
| WT + G125F | 39 | 8 | 92 |
| WT + A140V | 13 | 4 | 100 |

TABLE 1B-continued

Thermal stability and affinity of various single mutants of 3-HBDH

| Clone | Affinity for* | | Thermal Stability** |
|---|---|---|---|
| | 3-HB | cNAD | |
| WT + T144R | 40 | 13 | 100 |
| WT + A145G | 30 | 7 | 100 |
| WT + P195Q | 11 | 4 | 100 |
| WT + P195L | 10 | 5 | 96 |
| WT + Q197I | 21 | 5 | 100 |
| WT + Q217V | 22 | 3 | 100 |
| WT + A223V | 18 | 6 | 100 |
| WT + V232C | 41 | 11 | 100 |
| WT + V232Y | 31 | 4 | 100 |
| WT + V232W | 30 | 4 | 100 |
| WT + A239Y | 31 | 4 | 100 |
| WT + A239W | 30 | 4 | 100 |
| WT + V250M | 40 | 10 | 100 |
| WT + L257M | 34 | 10 | 100 |
| WT + L257Q | 22 | 7 | 100 |

*given as activity ratio (%) with 1.94/62.22 mM 3-HB and 0.032/4.15 mM cNAD
**given as remaining activity (%) after a 30 minute-incubation at 50° C.

Table shows that often improvement of thermal stability has an effect on affinity for substrate and/or cofactor. Four positions were found to improve both stability and affinity parameters: Positions 125, 144, 232 and 250 of SEQ ID NO: 1.

Exemplary mutant with exchange V250M was chosen for further optimization by combining of additional found positions.

Example 3 Screening of 3-HBDH Mutants from Second Round of Mutagenesis (Mutants with Amino Acid Substitution V250M/I and Optionally Further Amino Acid Substitution(s))

Unless indicated otherwise, the experiments have been carried out as detailed in Example 2. In a second round of mutagenesis selected substitutions were combined into variant WT+V250M. The results are summarized in Tables 2A and 2B:

TABLE 2A

Thermal stability (54° C., 30 min) and affinity of various mutants with amino acid substitution V250M or V250I

| Clone | Affinity for* | | Thermal Stability** |
|---|---|---|---|
| | 3-HB | cNAD | |
| WT | 33 | 9 | 0 (5 50° C.) |
| WT + V250I | 41 | nt | 0 (27 50° C.) |
| WT + V250M | 41 | 16 | 31 (83 50° C.) |
| WT + G230L + V250M | 37 | 8 | 75 |
| WT + F37Y + V250M | 40 | 17 | 33 |
| WT + A140V + V250M | 9 | 5 | 44 |
| WT + F37Y + G230L + V250M | 37 | 10 | 89 |
| WT + F37Y + A140V + V250M | 13 | 4 | 75 |
| WT + A140V + G230L + V250M | 13 | 5 | 80 |
| WT + D202G + G230L + V250M | 41 | 9 | 74 |

*given as activity ratio (%) with 1.94/62.22 mM 3-HB and 0.032/4.15 mM cNAD
**given as remaining activity (%) after a 30-minute incubation at 54° C. (unless indicated otherwise)
nt not tested Table 2A shows that multiple substitutions (in addition to V250M) show a further increased stability. Mutants WT+G230L+V250M, WT+F37Y+V250M, WT+F37Y+G230L+V250M and WT+D202G+G230L+V250M are of particular interest as they also show good affinity for 3-HB.

Exemplary variant WT+F37Y+G230L+V250M was further combined with other found positions. The results are summarized in Table 2B:

TABLE 2B

Thermal stability (64° C., 30 min) and affinity of various mutants with amino acid substitutions F37Y, G230L and V250M

| Clone | Affinity for* | | Thermal Stability** |
|---|---|---|---|
| | 3-HB | cNAD | |
| WT + F37Y + G230L + V250M | 36 | 4 | 7 |
| WT + F37Y + P195Q + G230L + V250M | 13 | 4 | 51 |
| WT + F37Y + A145G + G230L + V250M | 34 | 11 | 29 |

*given as activity ratio (%) with 1.94/62.22 mM 3-HB and 0.032/4.15 mM cNAD
**given as remaining activity (%) after a 30-minute incubation at 64° C.

Table 2B shows that stability of mutant WT+F37Y+G230L+V250M can be further increased by adding substitution P195Q or A145G, which show also acceptable affinity for 3-HB and cNAD.

```
                              SEQUENCES

WT: wild-type 3-HBDH from Rhodobacter sphaeroides (SEQ ID NO: 1)
MDLNGKRAIV  TGSNSGIGLG  CAEELARAGA  EVVINSFTDR  DEDHALAEKI  GREHGVSCRY   60

IAADMSDGEA  CRALIETAGG  CDILVNNAGI  QHVSSIEEFP  VGKWNAILAI  NLSSAFHTTA  120

AALPGMRAKG  WGRIVNIASA  HGLTASPYKS  AYVAAKHGVV  GFTKVTALET  AGKGITCNAI  180

CPGYVLTPLV  EAQIPDQMKA  HDMDRETVIR  EVMLDRQPSR  QFATTGQIGG  TVVFLCSGAA  240

DQITGTTISV  DGGWTAL                                                     257

WT + G125F (SEQ ID NO: 2)
MDLNGKRAIV  TGSNSGIGLG  CAEELARAGA  EVVINSFTDR  DEDHALAEKI  GREHGVSCRY   60

IAADMSDGEA  CRALIETAGG  CDILVNNAGI  QHVSSIEEFP  VGKWNAILAI  NLSSAFHTTA  120

AALPFMRAKG  WGRIVNIASA  HGLTASPYKS  AYVAAKHGVV  GFTKVTALET  AGKGITCNAI  180

CPGYVLTPLV  EAQIPDQMKA  HDMDRETVIR  EVMLDRQPSR  QFATTGQIGG  TVVFLCSGAA  240

DQITGTTISV  DGGWTAL                                                     257
```

SEQUENCES

```
WT + T144R (SEQ ID NO: 3)
MDLNGKRAIV TGSNSGIGLG CAEELARAGA EVVINSFTDR DEDHALAEKI GREHGVSCRY   60

IAADMSDGEA CRALIETAGG CDILVNNAGI QHVSSIEEFP VGKWNAILAI NLSSAFHTTA  120

AALPGMRAKG WGRIVNIASA HGLRASPYKS AYVAAKHGVV GFTKVTALET AGKGITCNAI  180

CPGYVLTPLV EAQIPDQMKA HDMDRETVIR EVMLDRQPSR QFATTGQIGG TVVFLCSGAA  240

DQITGTTISV DGGWTAL                                                 257

WT + V232C (SEQ ID NO: 4)
MDLNGKRAIV TGSNSGIGLG CAEELARAGA EVVINSFTDR DEDHALAEKI GREHGVSCRY   60

IAADMSDGEA CRALIETAGG CDILVNNAGI QHVSSIEEFP VGKWNAILAI NLSSAFHTTA  120

AALPGMRAKG WGRIVNIASA HGLTASPYKS AYVAAKHGVV GFTKVTALET AGKGITCNAI  180

CPGYVLTPLV EAQIPDQMKA HDMDRETVIR EVMLDRQPSR QFATTGQIGG TCVFLCSGAA  240

DQITGTTISV DGGWTAL                                                 257

WT + V250M (SEQ ID NO: 5)
MDLNGKRAIV TGSNSGIGLG CAEELARAGA EVVINSFTDR DEDHALAEKI GREHGVSCRY   60

IAADMSDGEA CRALIETAGG CDILVNNAGI QHVSSIEEFP VGKWNAILAI NLSSAFHTTA  120

AALPGMRAKG WGRIVNIASA HGLTASPYKS AYVAAKHGVV GFTKVTALET AGKGITCNAI  180

CPGYVLTPLV EAQIPDQMKA HDMDRETVIR EVMLDRQPSR QFATTGQIGG TVVFLCSGAA  240

DQITGTTISM DGGWTAL                                                 257

WT + G230L + V250M (SEQ ID NO: 6)
MDLNGKRAIV TGSNSGIGLG CAEELARAGA EVVINSFTDR DEDHALAEKI GREHGVSCRY   60

IAADMSDGEA CRALIETAGG CDILVNNAGI QHVSSIEEFP VGKWNAILAI NLSSAFHTTA  120

AALPGMRAKG WGRIVNIASA HGLTASPYKS AYVAAKHGVV GFTKVTALET AGKGITCNAI  180

CPGYVLTPLV EAQIPDQMKA HDMDRETVIR EVMLDRQPSR QFATTGQIGL TVVFLCSGAA  240

DQITGTTISM DGGWTAL                                                 257

WT + F37Y + V250M (SEQ ID NO: 7)
MDLNGKRAIV TGSNSGIGLG CAEELARAGA EVVINSYTDR DEDHALAEKI GREHGVSCRY   60

IAADMSDGEA CRALIETAGG CDILVNNAGI QHVSSIEEFP VGKWNAILAI NLSSAFHTTA  120

AALPGMRAKG WGRIVNIASA HGLTASPYKS AYVAAKHGVV GFTKVTALET AGKGITCNAI  180

CPGYVLTPLV EAQIPDQMKA HDMDRETVIR EVMLDRQPSR QFATTGQIGG TVVFLCSGAA  240

DQITGTTISM DGGWTAL                                                 257

WT + F37Y + G230L + V250M (SEQ ID NO: 8)
MDLNGKRAIV TGSNSGIGLG CAEELARAGA EVVINSYTDR DEDHALAEKI GREHGVSCRY   60

IAADMSDGEA CRALIETAGG CDILVNNAGI QHVSSIEEFP VGKWNAILAI NLSSAFHTTA  120

AALPGMRAKG WGRIVNIASA HGLTASPYKS AYVAAKHGVV GFTKVTALET AGKGITCNAI  180

CPGYVLTPLV EAQIPDQMKA HDMDRETVIR EVMLDRQPSR QFATTGQIGL TVVFLCSGAA  240

DQITGTTISM DGGWTAL                                                 257

WT + D202G + G230L + V250M (SEQ ID NO: 9)
MDLNGKRAIV TGSNSGIGLG CAEELARAGA EVVINSFTDR DEDHALAEKI GREHGVSCRY   60

IAADMSDGEA CRALIETAGG CDILVNNAGI QHVSSIEEFP VGKWNAILAI NLSSAFHTTA  120

AALPGMRAKG WGRIVNIASA HGLTASPYKS AYVAAKHGVV GFTKVTALET AGKGITCNAI  180

CPGYVLTPLV EAQIPDQMKA HGMDRETVIR EVMLDRQPSR QFATTGQIGL TVVFLCSGAA  240

DQITGTTISM DGGWTAL                                                 257
```

| SEQUENCES |
|---|
| WT + F37Y + A145G + G230L + V250M (SEQ ID NO: 10) |
| MDLNGKRAIV TGSNSGIGLG CAEELARAGA EVVINSYTDR DEDHALAEKI GREHGVSCRY 60 |
| IAADMSDGEA CRALIETAGG CDILVNNAGI QHVSSIEEFP VGKWNAILAI NLSSAFHTTA 120 |
| AALPGMRAKG WGRIVNIASA HGLTGSPYKS AYVAAKHGVV GFTKVTALET AGKGITCNAI 180 |
| CPGYVLTPLV EAQIPDQMKA HDMDRETVIR EVMLDRQPSR QFATTGQIGL TVVFLCSGAA 240 |
| DQITGTTISM DGGWTAL 257 |
| WT + F37Y + P195Q + G230L + V250M (SEQ ID NO: 11) |
| MDLNGKRAIV TGSNSGIGLG CAEELARAGA EVVINSYTDR DEDHALAEKI GREHGVSCRY 60 |
| IAADMSDGEA CRALIETAGG CDILVNNAGI QHVSSIEEFP VGKWNAILAI NLSSAFHTTA 120 |
| AALPGMRAKG WGRIVNIASA HGLTASPYKS AYVAAKHGVV GFTKVTALET AGKGITCNAI 180 |
| CPGYVLTPLV EAQIQDQMKA HDMDRETVIR EVMLDRQPSR QFATTGQIGL TVVFLCSGAA 240 |
| DQITGTTISM DGGWTAL 257 |

The invention claimed is:

1. A mutant 3-hydroxybutyrate dehydrogenase (3-HBDH) from *Rhodobacter sphaeroides* with improved performance relative to the wild-type 3-HBDH, wherein the mutant comprises an amino acid sequence that is at least 80% identical to the amino acid sequence of SEQ ID NO: 1 (wild type 3-HBDH from *Rhodobacter sphaeroides*) and wherein the mutant has at least one amino acid substitution relative to the wild-type 3-HBDH at a position corresponding to position 250 of SEQ ID NO: 1, wherein, the improved performance is at least increased thermal stability relative to the wild-type 3-HBDH.

2. The mutant 3-HBDH of claim 1, wherein the amino acid at the position corresponding to position 250 of SEQ ID NO: 1 is substituted with Met (250Met) or Ile (250Ile).

3. The mutant 3-HBDH of claim 1, wherein the mutant has at least one further amino acid substitution at one or more of the position(s) corresponding to position(s) 66, 109, 113, 125, 140, 144, 145, 195, 197, 217, 223, 232, 239 and/or 257 of SEQ ID NO: 1.

4. The mutant 3-HBDH of claim 3, wherein the amino acid at the position corresponding to
  position 66 of SEQ ID NO: 1 is substituted with Tyr (66Tyr), or Asn (66Asn);
  position 109 of SEQ ID NO: 1 is substituted with Glu (109Glu);
  position 113 of SEQ ID NO: 1 is substituted with Thr (113Thr);
  position 125 of SEQ ID NO: 1 is substituted with Phe (125Phe);
  position 140 of SEQ ID NO: 1 is substituted with Val (140Val);
  position 144 of SEQ ID NO: 1 is substituted with Arg (144Arg);

position 145 of SEQ ID NO: 1 is substituted with Gly (145Gly);
position 195 of SEQ ID NO: 1 is substituted with Gln (195Gln) or Leu (195Leu);
position 197 of SEQ ID NO: 1 is substituted with Ile (197Ile);
position 217 of SEQ ID NO: 1 is substituted with Val (217Val);
position 223 of SEQ ID NO: 1 is substituted with Val (223Val);
position 232 of SEQ ID NO: 1 is substituted with Cys (232Cys), Tyr (232Tyr), or Trp (232Trp);
position 239 of SEQ ID NO: 1 is substituted with Tyr (239Tyr), or Trp (239Trp);
position 250 of SEQ ID NO: 1 is substituted with Met (250Met); and/or
position 257 of SEQ ID NO: 1 is substituted with Met (257Met) or Gln (257Gln).

5. The mutant of claim 4, wherein the amino acid at the position corresponding to
position 37 of SEQ ID NO: 1 is substituted with Tyr (37Tyr);
position 202 of SEQ ID NO: 1 is substituted with Gly (202Gly), and/or
position 230 of SEQ ID NO: 1 is substituted with Leu (230Leu).

6. The mutant 3-HBDH of claim 3,
wherein the mutant 3-HBDH has one or more mutation selected from:
125Phe;
144Arg;
232Cys;
250Met;
230Leu and 250Met;
37Tyr and 250Met;
37Tyr, 230Leu and 250Met;
202Gly, 230Leu and 250Met;
37Tyr, 145Gly, 230Leu and 250Met; and/or
37Tyr, 195Gln, 230Leu and 250Met
corresponding to positions of SEQ ID NO:1.

7. The mutant 3-HBDH of claim 1, wherein the mutant 3-HBDH comprises an amino acid sequence that is at least 85%, 90%, 95%, 96%, 97%, 98%, or 99% identical to the amino acid sequence of any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, or SEQ ID NO: 11.

8. The mutant 3-HBDH of claim 1, wherein improved performance relative to the wild-type 3-HBDH further comprises
increased substrate affinity, for 3-hydroxybutyrate, relative to the wild-type 3-HBDH; and/or
increased cofactor affinity, for NAD or a derivative thereof, wherein the derivate is carba-NAD, relative to the wild-type 3-HBDH.

9. The mutant 3-HBDH of claim 8,
wherein the mutant 3-HBDH has an at least 2-fold increased stability relative to the wild-type 3-HBDH, an at least 3-fold increased stability, an at least 4-fold increased stability, or an at least 5-fold increased stability; and/or
wherein the mutant 3-HBDH has an increased substrate and/or cofactor affinity relative to the wild-type 3-HBDH, an increased affinity for (i) 3-hydroxybutyrate and/or (ii) nicotinamide adenine dinucleotide (NAD) or a functionally active derivative thereof and/or wherein the substrate and/or cofactor affinity is increased by at least 5%, at least 10%, at least 15%, or at least 20%.

10. A nucleic acid encoding the mutant 3-HBDH of claim 1.

11. A cell comprising the mutant 3-HBDH of claim 1 or the nucleic acid of claim 10.

12. A method of determining the amount or concentration of 3-hydroxybutyrate in a sample, the method comprising
a) contacting the sample with the mutant 3-HBDH of claim 1 under conditions conducive to the activity of the 3-HBDH;
b) reacting 3-hydroxybutyrate with nicotinamide adenine dinucleotide (NAD) or a functionally active derivative thereof; and
c) determining the change in the redox state of NAD or the derivative thereof;
thereby determining the amount or concentration of 3-hydroxybutyrate in the sample.

13. The method of claim 12,
a) wherein the determining of the change in the redox state of NAD or the derivate thereof includes the determination of the concentration of (i) NAD or the derivate thereof and/or (ii) NADH or the derivate thereof; and/or
b) wherein the determining the change in the redox state of NAD or the derivative thereof is electrochemically or optically; and/or
c) wherein the method further comprises determining the amount or concentration of acetoacetate and/or acetone; and/or
d) wherein the method further comprises determining the amount or concentration of glucose; and/or
e) wherein the functionally active derivative of NAD is carba-NAD; and/or
f) wherein the mutant 3-HBDH is part of a sensor, a test strip, a test element, a test strip device or a liquid test; and/or
g) wherein the sample is a body fluid.

14. A device for determining the amount or concentration of 3-hydroxybutyrate in a sample comprising the mutant 3-HBDH according to claim 1 and a further component required for said determining.

15. The device according to claim 14,
a) wherein the device is selected from the group consisting of a sensor or a test strip; and/or
b) wherein the device further allows for determining the amount or concentration of glucose in the sample.

16. The mutant of 3-HBDH according to claim 2, wherein the mutant 3-HBDH has only a mutation selected from:
250Met;
230Leu and 250Met;
37Tyr and 250Met;
37Tyr, 230Leu and 250Met;
202Gly, 230Leu and 250Met;
37Tyr, 145Gly, 230Leu and 250Met; or
37Tyr, 195Gln, 230Leu and 250Met corresponding to positions of SEQ ID NO: 1.

17. The mutant of 3-HBFB according to claim 7, wherein the mutant 3-HBDH comprises a sequence selected from the group consisting of SEQ ID NO: 5, SEQ ID NO: 6, SEQ ID NO: 7, SEQ ID NO: 8, SEQ ID NO: 9, SEQ ID NO: 10, or SEQ ID NO: 11.

18. The mutant of 3-HBFB according to claim 7, wherein the mutant 3-HBDH consists of a sequence selected from the group consisting of SEQ ID NO: 5, SEQ ID NO: 6, SEQ ID NO: 7, SEQ ID NO: 8, SEQ ID NO: 9, SEQ ID NO: 10, or SEQ ID NO: 11.

19. The mutant 3-HBDH of claim 1, wherein the amino acid at the position corresponding to position 250 of SEQ ID NO: 1 is substituted with Met (250Met).

20. The device according to claim 15, wherein the sensor is an electrochemical sensor or an optical sensor.

\* \* \* \* \*

SEQUENCE LISTING

<160> NUMBER OF SEQ ID NOS: 11

<210> SEQ ID NO 1
<211> LENGTH: 257
<212> TYPE: PRT
<213> ORGANISM: Rhodobacter sphaeroides

<400> SEQUENCE: 1

Met Asp Leu Asn Gly Lys Arg Ala Ile Val Thr Gly Ser Asn Ser Gly
1               5                   10                  15

Ile Gly Leu Gly Cys Ala Glu Glu Leu Ala Arg Ala Gly Ala Glu Val
            20                  25                  30

Val Ile Asn Ser Phe Thr Asp Arg Asp Glu Asp His Ala Leu Ala Glu
        35                  40                  45

Lys Ile Gly Arg Glu His Gly Val Ser Cys Arg Tyr Ile Ala Ala Asp
    50                  55                  60

Met Ser Asp Gly Glu Ala Cys Arg Ala Leu Ile Glu Thr Ala Gly Gly
65                  70                  75                  80

Cys Asp Ile Leu Val Asn Asn Ala Gly Ile Gln His Val Ser Ser Ile
                85                  90                  95

Glu Glu Phe Pro Val Gly Lys Trp Asn Ala Ile Leu Ala Ile Asn Leu
            100                 105                 110

Ser Ser Ala Phe His Thr Thr Ala Ala Ala Leu Pro Gly Met Arg Ala
        115                 120                 125

Lys Gly Trp Gly Arg Ile Val Asn Ile Ala Ser Ala His Gly Leu Thr
    130                 135                 140

Ala Ser Pro Tyr Lys Ser Ala Tyr Val Ala Ala Lys His Gly Val Val
145                 150                 155                 160

Gly Phe Thr Lys Val Thr Ala Leu Glu Thr Ala Gly Lys Gly Ile Thr
                165                 170                 175

Cys Asn Ala Ile Cys Pro Gly Tyr Val Leu Thr Pro Leu Val Glu Ala
            180                 185                 190

Gln Ile Pro Asp Gln Met Lys Ala His Asp Met Asp Arg Glu Thr Val
        195                 200                 205

Ile Arg Glu Val Met Leu Asp Arg Gln Pro Ser Arg Gln Phe Ala Thr

```
                210                 215                 220
Thr Gly Gln Ile Gly Gly Thr Val Val Phe Leu Cys Ser Gly Ala Ala
225                 230                 235                 240

Asp Gln Ile Thr Gly Thr Thr Ile Ser Val Asp Gly Gly Trp Thr Ala
                245                 250                 255

Leu

<210> SEQ ID NO 2
<211> LENGTH: 257
<212> TYPE: PRT
<213> ORGANISM: Artificial Sequence
<220> FEATURE:
<223> OTHER INFORMATION: Mutant 3-HBDH

<400> SEQUENCE: 2

Met Asp Leu Asn Gly Lys Arg Ala Ile Val Thr Gly Ser Asn Ser Gly
1               5                   10                  15

Ile Gly Leu Gly Cys Ala Glu Glu Leu Ala Arg Ala Gly Ala Glu Val
                20                  25                  30

Val Ile Asn Ser Phe Thr Asp Arg Asp Glu Asp His Ala Leu Ala Glu
            35                  40                  45

Lys Ile Gly Arg Glu His Gly Val Ser Cys Arg Tyr Ile Ala Ala Asp
    50                  55                  60

Met Ser Asp Gly Glu Ala Cys Arg Ala Leu Ile Glu Thr Ala Gly Gly
65                  70                  75                  80

Cys Asp Ile Leu Val Asn Asn Ala Gly Ile Gln His Val Ser Ser Ile
                85                  90                  95

Glu Glu Phe Pro Val Gly Lys Trp Asn Ala Ile Leu Ala Ile Asn Leu
                100                 105                 110

Ser Ser Ala Phe His Thr Thr Ala Ala Leu Pro Phe Met Arg Ala
            115                 120                 125

Lys Gly Trp Gly Arg Ile Val Asn Ile Ala Ser Ala His Gly Leu Thr
    130                 135                 140

Ala Ser Pro Tyr Lys Ser Ala Tyr Val Ala Ala Lys His Gly Val Val
145                 150                 155                 160

Gly Phe Thr Lys Val Thr Ala Leu Glu Thr Ala Gly Lys Gly Ile Thr
                165                 170                 175

Cys Asn Ala Ile Cys Pro Gly Tyr Val Leu Thr Pro Leu Val Glu Ala
            180                 185                 190

Gln Ile Pro Asp Gln Met Lys Ala His Asp Met Asp Arg Glu Thr Val
    195                 200                 205

Ile Arg Glu Val Met Leu Asp Arg Gln Pro Ser Arg Gln Phe Ala Thr
210                 215                 220

Thr Gly Gln Ile Gly Gly Thr Val Val Phe Leu Cys Ser Gly Ala Ala
225                 230                 235                 240

Asp Gln Ile Thr Gly Thr Thr Ile Ser Val Asp Gly Gly Trp Thr Ala
                245                 250                 255

Leu

<210> SEQ ID NO 3
<211> LENGTH: 257
<212> TYPE: PRT
<213> ORGANISM: Artificial Sequence
<220> FEATURE:
<223> OTHER INFORMATION: Mutant 3-HBDH

<400> SEQUENCE: 3
```

```
Met Asp Leu Asn Gly Lys Arg Ala Ile Val Thr Gly Ser Asn Ser Gly
1               5                   10                  15

Ile Gly Leu Gly Cys Ala Glu Glu Leu Ala Arg Ala Gly Ala Glu Val
            20                  25                  30

Val Ile Asn Ser Phe Thr Asp Arg Asp Glu Asp His Ala Leu Ala Glu
            35                  40                  45

Lys Ile Gly Arg Glu His Gly Val Ser Cys Arg Tyr Ile Ala Ala Asp
        50                  55                  60

Met Ser Asp Gly Glu Ala Cys Arg Ala Leu Ile Glu Thr Ala Gly Gly
65                  70                  75                  80

Cys Asp Ile Leu Val Asn Asn Ala Gly Ile Gln His Val Ser Ser Ile
                85                  90                  95

Glu Glu Phe Pro Val Gly Lys Trp Asn Ala Ile Leu Ala Ile Asn Leu
            100                 105                 110

Ser Ser Ala Phe His Thr Thr Ala Ala Leu Pro Gly Met Arg Ala
            115                 120                 125

Lys Gly Trp Gly Arg Ile Val Asn Ile Ala Ser Ala His Gly Leu Arg
        130                 135                 140

Ala Ser Pro Tyr Lys Ser Ala Tyr Val Ala Ala Lys His Gly Val Val
145                 150                 155                 160

Gly Phe Thr Lys Val Thr Ala Leu Glu Thr Ala Gly Lys Gly Ile Thr
                165                 170                 175

Cys Asn Ala Ile Cys Pro Gly Tyr Val Leu Thr Pro Leu Val Glu Ala
            180                 185                 190

Gln Ile Pro Asp Gln Met Lys Ala His Asp Met Asp Arg Glu Thr Val
        195                 200                 205

Ile Arg Glu Val Met Leu Asp Arg Gln Pro Ser Arg Gln Phe Ala Thr
    210                 215                 220

Thr Gly Gln Ile Gly Gly Thr Val Val Phe Leu Cys Ser Gly Ala Ala
225                 230                 235                 240

Asp Gln Ile Thr Gly Thr Thr Ile Ser Val Asp Gly Gly Trp Thr Ala
                245                 250                 255

Leu
```

<210> SEQ ID NO 4
<211> LENGTH: 257
<212> TYPE: PRT
<213> ORGANISM: Artificial Sequence
<220> FEATURE:
<223> OTHER INFORMATION: Mutant 3-HBDH

<400> SEQUENCE: 4

```
Met Asp Leu Asn Gly Lys Arg Ala Ile Val Thr Gly Ser Asn Ser Gly
1               5                   10                  15

Ile Gly Leu Gly Cys Ala Glu Glu Leu Ala Arg Ala Gly Ala Glu Val
            20                  25                  30

Val Ile Asn Ser Phe Thr Asp Arg Asp Glu Asp His Ala Leu Ala Glu
            35                  40                  45

Lys Ile Gly Arg Glu His Gly Val Ser Cys Arg Tyr Ile Ala Ala Asp
        50                  55                  60

Met Ser Asp Gly Glu Ala Cys Arg Ala Leu Ile Glu Thr Ala Gly Gly
65                  70                  75                  80

Cys Asp Ile Leu Val Asn Asn Ala Gly Ile Gln His Val Ser Ser Ile
                85                  90                  95
```

```
Glu Glu Phe Pro Val Gly Lys Trp Asn Ala Ile Leu Ala Ile Asn Leu
            100                 105                 110

Ser Ser Ala Phe His Thr Thr Ala Ala Ala Leu Pro Gly Met Arg Ala
            115                 120                 125

Lys Gly Trp Gly Arg Ile Val Asn Ile Ala Ser Ala His Gly Leu Thr
        130                 135                 140

Ala Ser Pro Tyr Lys Ser Ala Tyr Val Ala Ala Lys His Gly Val Val
145                 150                 155                 160

Gly Phe Thr Lys Val Thr Ala Leu Glu Thr Ala Gly Lys Gly Ile Thr
                165                 170                 175

Cys Asn Ala Ile Cys Pro Gly Tyr Val Leu Thr Pro Leu Val Glu Ala
                180                 185                 190

Gln Ile Pro Asp Gln Met Lys Ala His Asp Met Asp Arg Glu Thr Val
            195                 200                 205

Ile Arg Glu Val Met Leu Asp Arg Gln Pro Ser Arg Gln Phe Ala Thr
        210                 215                 220

Thr Gly Gln Ile Gly Gly Thr Cys Val Phe Leu Cys Ser Gly Ala Ala
225                 230                 235                 240

Asp Gln Ile Thr Gly Thr Thr Ile Ser Val Asp Gly Gly Trp Thr Ala
                245                 250                 255

Leu
```

```
<210> SEQ ID NO 5
<211> LENGTH: 257
<212> TYPE: PRT
<213> ORGANISM: Artificial Sequence
<220> FEATURE:
<223> OTHER INFORMATION: Mutant 3-HBDH

<400> SEQUENCE: 5
```

```
Met Asp Leu Asn Gly Lys Arg Ala Ile Val Thr Gly Ser Asn Ser Gly
1               5                   10                  15

Ile Gly Leu Gly Cys Ala Glu Glu Leu Ala Arg Ala Gly Ala Glu Val
            20                  25                  30

Val Ile Asn Ser Phe Thr Asp Arg Asp Glu Asp His Ala Leu Ala Glu
        35                  40                  45

Lys Ile Gly Arg Glu His Gly Val Ser Cys Arg Tyr Ile Ala Ala Asp
    50                  55                  60

Met Ser Asp Gly Glu Ala Cys Arg Ala Leu Ile Glu Thr Ala Gly Gly
65                  70                  75                  80

Cys Asp Ile Leu Val Asn Asn Ala Gly Ile Gln His Val Ser Ser Ile
                85                  90                  95

Glu Glu Phe Pro Val Gly Lys Trp Asn Ala Ile Leu Ala Ile Asn Leu
            100                 105                 110

Ser Ser Ala Phe His Thr Thr Ala Ala Ala Leu Pro Gly Met Arg Ala
            115                 120                 125

Lys Gly Trp Gly Arg Ile Val Asn Ile Ala Ser Ala His Gly Leu Thr
        130                 135                 140

Ala Ser Pro Tyr Lys Ser Ala Tyr Val Ala Ala Lys His Gly Val Val
145                 150                 155                 160

Gly Phe Thr Lys Val Thr Ala Leu Glu Thr Ala Gly Lys Gly Ile Thr
                165                 170                 175

Cys Asn Ala Ile Cys Pro Gly Tyr Val Leu Thr Pro Leu Val Glu Ala
                180                 185                 190

Gln Ile Pro Asp Gln Met Lys Ala His Asp Met Asp Arg Glu Thr Val
```

```
                195                 200                 205
Ile Arg Glu Val Met Leu Asp Arg Gln Pro Ser Arg Gln Phe Ala Thr
    210                 215                 220

Thr Gly Gln Ile Gly Gly Thr Val Val Phe Leu Cys Ser Gly Ala Ala
225                 230                 235                 240

Asp Gln Ile Thr Gly Thr Thr Ile Ser Met Asp Gly Gly Trp Thr Ala
                245                 250                 255

Leu

<210> SEQ ID NO 6
<211> LENGTH: 257
<212> TYPE: PRT
<213> ORGANISM: Artificial Sequence
<220> FEATURE:
<223> OTHER INFORMATION: Mutant 3-HBDH

<400> SEQUENCE: 6

Met Asp Leu Asn Gly Lys Arg Ala Ile Val Thr Gly Ser Asn Ser Gly
1               5                   10                  15

Ile Gly Leu Gly Cys Ala Glu Glu Leu Ala Arg Ala Gly Ala Glu Val
            20                  25                  30

Val Ile Asn Ser Phe Thr Asp Arg Asp Glu Asp His Ala Leu Ala Glu
        35                  40                  45

Lys Ile Gly Arg Glu His Gly Val Ser Cys Arg Tyr Ile Ala Ala Asp
    50                  55                  60

Met Ser Asp Gly Glu Ala Cys Arg Ala Leu Ile Glu Thr Ala Gly Gly
65                  70                  75                  80

Cys Asp Ile Leu Val Asn Asn Ala Gly Ile Gln His Val Ser Ser Ile
                85                  90                  95

Glu Glu Phe Pro Val Gly Lys Trp Asn Ala Ile Leu Ala Ile Asn Leu
            100                 105                 110

Ser Ser Ala Phe His Thr Thr Ala Ala Leu Pro Gly Met Arg Ala
        115                 120                 125

Lys Gly Trp Gly Arg Ile Val Asn Ile Ala Ser Ala His Gly Leu Thr
    130                 135                 140

Ala Ser Pro Tyr Lys Ser Ala Tyr Val Ala Ala Lys His Gly Val Val
145                 150                 155                 160

Gly Phe Thr Lys Val Thr Ala Leu Glu Thr Ala Gly Lys Gly Ile Thr
                165                 170                 175

Cys Asn Ala Ile Cys Pro Gly Tyr Val Leu Thr Pro Leu Val Glu Ala
            180                 185                 190

Gln Ile Pro Asp Gln Met Lys Ala His Asp Met Asp Arg Glu Thr Val
        195                 200                 205

Ile Arg Glu Val Met Leu Asp Arg Gln Pro Ser Arg Gln Phe Ala Thr
    210                 215                 220

Thr Gly Gln Ile Gly Leu Thr Val Val Phe Leu Cys Ser Gly Ala Ala
225                 230                 235                 240

Asp Gln Ile Thr Gly Thr Thr Ile Ser Met Asp Gly Gly Trp Thr Ala
                245                 250                 255

Leu

<210> SEQ ID NO 7
<211> LENGTH: 257
<212> TYPE: PRT
<213> ORGANISM: Artificial Sequence
<220> FEATURE:
```

<223> OTHER INFORMATION: Mutant 3-HBDH

<400> SEQUENCE: 7

```
Met Asp Leu Asn Gly Lys Arg Ala Ile Val Thr Gly Ser Asn Ser Gly
1               5                   10                  15
Ile Gly Leu Gly Cys Ala Glu Glu Leu Ala Arg Ala Gly Ala Glu Val
            20                  25                  30
Val Ile Asn Ser Tyr Thr Asp Arg Asp Glu Asp His Ala Leu Ala Glu
        35                  40                  45
Lys Ile Gly Arg Glu His Gly Val Ser Cys Arg Tyr Ile Ala Ala Asp
    50                  55                  60
Met Ser Asp Gly Glu Ala Cys Arg Ala Leu Ile Glu Thr Ala Gly Gly
65                  70                  75                  80
Cys Asp Ile Leu Val Asn Asn Ala Gly Ile Gln His Val Ser Ser Ile
                85                  90                  95
Glu Glu Phe Pro Val Gly Lys Trp Asn Ala Ile Leu Ala Ile Asn Leu
            100                 105                 110
Ser Ser Ala Phe His Thr Thr Ala Ala Ala Leu Pro Gly Met Arg Ala
        115                 120                 125
Lys Gly Trp Gly Arg Ile Val Asn Ile Ala Ser Ala His Gly Leu Thr
    130                 135                 140
Ala Ser Pro Tyr Lys Ser Ala Tyr Val Ala Ala Lys His Gly Val Val
145                 150                 155                 160
Gly Phe Thr Lys Val Thr Ala Leu Glu Thr Ala Gly Lys Gly Ile Thr
                165                 170                 175
Cys Asn Ala Ile Cys Pro Gly Tyr Val Leu Thr Pro Leu Val Glu Ala
            180                 185                 190
Gln Ile Pro Asp Gln Met Lys Ala His Asp Met Asp Arg Glu Thr Val
        195                 200                 205
Ile Arg Glu Val Met Leu Asp Arg Gln Pro Ser Arg Gln Phe Ala Thr
    210                 215                 220
Thr Gly Gln Ile Gly Gly Thr Val Val Phe Leu Cys Ser Gly Ala Ala
225                 230                 235                 240
Asp Gln Ile Thr Gly Thr Thr Ile Ser Met Asp Gly Trp Thr Ala
                245                 250                 255
Leu
```

<210> SEQ ID NO 8
<211> LENGTH: 257
<212> TYPE: PRT
<213> ORGANISM: Artificial Sequence
<220> FEATURE:
<223> OTHER INFORMATION: Mutant 3-HBDH

<400> SEQUENCE: 8

```
Met Asp Leu Asn Gly Lys Arg Ala Ile Val Thr Gly Ser Asn Ser Gly
1               5                   10                  15
Ile Gly Leu Gly Cys Ala Glu Glu Leu Ala Arg Ala Gly Ala Glu Val
            20                  25                  30
Val Ile Asn Ser Tyr Thr Asp Arg Asp Glu Asp His Ala Leu Ala Glu
        35                  40                  45
Lys Ile Gly Arg Glu His Gly Val Ser Cys Arg Tyr Ile Ala Ala Asp
    50                  55                  60
Met Ser Asp Gly Glu Ala Cys Arg Ala Leu Ile Glu Thr Ala Gly Gly
65                  70                  75                  80
```

```
Cys Asp Ile Leu Val Asn Asn Ala Gly Ile Gln His Val Ser Ser Ile
                85                  90                  95

Glu Glu Phe Pro Val Gly Lys Trp Asn Ala Ile Leu Ala Ile Asn Leu
            100                 105                 110

Ser Ser Ala Phe His Thr Thr Ala Ala Leu Pro Gly Met Arg Ala
        115                 120                 125

Lys Gly Trp Gly Arg Ile Val Asn Ile Ala Ser Ala His Gly Leu Thr
    130                 135                 140

Ala Ser Pro Tyr Lys Ser Ala Tyr Val Ala Lys His Gly Val Val
145                 150                 155                 160

Gly Phe Thr Lys Val Thr Ala Leu Glu Thr Ala Gly Lys Gly Ile Thr
                165                 170                 175

Cys Asn Ala Ile Cys Pro Gly Tyr Val Leu Thr Pro Leu Val Glu Ala
            180                 185                 190

Gln Ile Pro Asp Gln Met Lys Ala His Asp Met Asp Arg Glu Thr Val
        195                 200                 205

Ile Arg Glu Val Met Leu Asp Arg Gln Pro Ser Arg Gln Phe Ala Thr
    210                 215                 220

Thr Gly Gln Ile Gly Leu Thr Val Val Phe Leu Cys Ser Gly Ala Ala
225                 230                 235                 240

Asp Gln Ile Thr Gly Thr Thr Ile Ser Met Asp Gly Gly Trp Thr Ala
                245                 250                 255

Leu

<210> SEQ ID NO 9
<211> LENGTH: 257
<212> TYPE: PRT
<213> ORGANISM: Artificial Sequence
<220> FEATURE:
<223> OTHER INFORMATION: Mutant 3-HBDH

<400> SEQUENCE: 9

Met Asp Leu Asn Gly Lys Arg Ala Ile Val Thr Gly Ser Asn Ser Gly
1               5                   10                  15

Ile Gly Leu Gly Cys Ala Glu Glu Leu Ala Arg Ala Gly Ala Glu Val
            20                  25                  30

Val Ile Asn Ser Phe Thr Asp Arg Asp Glu Asp His Ala Leu Ala Glu
        35                  40                  45

Lys Ile Gly Arg Glu His Gly Val Ser Cys Arg Tyr Ile Ala Ala Asp
    50                  55                  60

Met Ser Asp Gly Glu Ala Cys Arg Ala Leu Ile Glu Thr Ala Gly Gly
65                  70                  75                  80

Cys Asp Ile Leu Val Asn Asn Ala Gly Ile Gln His Val Ser Ser Ile
                85                  90                  95

Glu Glu Phe Pro Val Gly Lys Trp Asn Ala Ile Leu Ala Ile Asn Leu
            100                 105                 110

Ser Ser Ala Phe His Thr Thr Ala Ala Leu Pro Gly Met Arg Ala
        115                 120                 125

Lys Gly Trp Gly Arg Ile Val Asn Ile Ala Ser Ala His Gly Leu Thr
    130                 135                 140

Ala Ser Pro Tyr Lys Ser Ala Tyr Val Ala Lys His Gly Val Val
145                 150                 155                 160

Gly Phe Thr Lys Val Thr Ala Leu Glu Thr Ala Gly Lys Gly Ile Thr
                165                 170                 175

Cys Asn Ala Ile Cys Pro Gly Tyr Val Leu Thr Pro Leu Val Glu Ala
```

```
                180                 185                 190
Gln Ile Pro Asp Gln Met Lys Ala His Gly Met Asp Arg Glu Thr Val
            195                 200                 205
Ile Arg Glu Val Met Leu Asp Arg Gln Pro Ser Arg Gln Phe Ala Thr
        210                 215                 220
Thr Gly Gln Ile Gly Leu Thr Val Val Phe Leu Cys Ser Gly Ala Ala
225                 230                 235                 240
Asp Gln Ile Thr Gly Thr Thr Ile Ser Met Asp Gly Gly Trp Thr Ala
                245                 250                 255
Leu
```

<210> SEQ ID NO 10
<211> LENGTH: 257
<212> TYPE: PRT
<213> ORGANISM: Artificial Sequence
<220> FEATURE:
<223> OTHER INFORMATION: Mutant 3-HBDH

<400> SEQUENCE: 10

```
Met Asp Leu Asn Gly Lys Arg Ala Ile Val Thr Gly Ser Asn Ser Gly
1               5                   10                  15
Ile Gly Leu Gly Cys Ala Glu Glu Leu Ala Arg Ala Gly Ala Glu Val
            20                  25                  30
Val Ile Asn Ser Tyr Thr Asp Arg Asp Glu Asp His Ala Leu Ala Glu
        35                  40                  45
Lys Ile Gly Arg Glu His Gly Val Ser Cys Arg Tyr Ile Ala Ala Asp
    50                  55                  60
Met Ser Asp Gly Glu Ala Cys Arg Ala Leu Ile Glu Thr Ala Gly Gly
65                  70                  75                  80
Cys Asp Ile Leu Val Asn Asn Ala Gly Ile Gln His Val Ser Ser Ile
                85                  90                  95
Glu Glu Phe Pro Val Gly Lys Trp Asn Ala Ile Leu Ala Ile Asn Leu
            100                 105                 110
Ser Ser Ala Phe His Thr Thr Ala Ala Leu Pro Gly Met Arg Ala
        115                 120                 125
Lys Gly Trp Gly Arg Ile Val Asn Ile Ala Ser Ala His Gly Leu Thr
    130                 135                 140
Gly Ser Pro Tyr Lys Ser Ala Tyr Val Ala Ala Lys His Gly Val Val
145                 150                 155                 160
Gly Phe Thr Lys Val Thr Ala Leu Glu Thr Ala Gly Lys Gly Ile Thr
                165                 170                 175
Cys Asn Ala Ile Cys Pro Gly Tyr Val Leu Thr Pro Leu Val Glu Ala
            180                 185                 190
Gln Ile Pro Asp Gln Met Lys Ala His Asp Met Asp Arg Glu Thr Val
        195                 200                 205
Ile Arg Glu Val Met Leu Asp Arg Gln Pro Ser Arg Gln Phe Ala Thr
    210                 215                 220
Thr Gly Gln Ile Gly Leu Thr Val Val Phe Leu Cys Ser Gly Ala Ala
225                 230                 235                 240
Asp Gln Ile Thr Gly Thr Thr Ile Ser Met Asp Gly Gly Trp Thr Ala
                245                 250                 255
Leu
```

<210> SEQ ID NO 11
<211> LENGTH: 257

```
<212> TYPE: PRT
<213> ORGANISM: Artificial Sequence
<220> FEATURE:
<223> OTHER INFORMATION: Mutant 3-HBDH

<400> SEQUENCE: 11

Met Asp Leu Asn Gly Lys Arg Ala Ile Val Thr Gly Ser Asn Ser Gly
1               5                   10                  15

Ile Gly Leu Gly Cys Ala Glu Glu Leu Ala Arg Ala Gly Ala Glu Val
                20                  25                  30

Val Ile Asn Ser Tyr Thr Asp Arg Asp Glu Asp His Ala Leu Ala Glu
            35                  40                  45

Lys Ile Gly Arg Glu His Gly Val Ser Cys Arg Tyr Ile Ala Ala Asp
    50                  55                  60

Met Ser Asp Gly Glu Ala Cys Arg Ala Leu Ile Glu Thr Ala Gly Gly
65                  70                  75                  80

Cys Asp Ile Leu Val Asn Asn Ala Gly Ile Gln His Val Ser Ser Ile
                85                  90                  95

Glu Glu Phe Pro Val Gly Lys Trp Asn Ala Ile Leu Ala Ile Asn Leu
                100                 105                 110

Ser Ser Ala Phe His Thr Thr Ala Ala Ala Leu Pro Gly Met Arg Ala
                115                 120                 125

Lys Gly Trp Gly Arg Ile Val Asn Ile Ala Ser Ala His Gly Leu Thr
    130                 135                 140

Ala Ser Pro Tyr Lys Ser Ala Tyr Val Ala Ala Lys His Gly Val Val
145                 150                 155                 160

Gly Phe Thr Lys Val Thr Ala Leu Glu Thr Ala Gly Lys Gly Ile Thr
                165                 170                 175

Cys Asn Ala Ile Cys Pro Gly Tyr Val Leu Thr Pro Leu Val Glu Ala
                180                 185                 190

Gln Ile Gln Asp Gln Met Lys Ala His Asp Met Asp Arg Glu Thr Val
    195                 200                 205

Ile Arg Glu Val Met Leu Asp Arg Gln Pro Ser Arg Gln Phe Ala Thr
    210                 215                 220

Thr Gly Gln Ile Gly Leu Thr Val Val Phe Leu Cys Ser Gly Ala Ala
225                 230                 235                 240

Asp Gln Ile Thr Gly Thr Thr Ile Ser Met Asp Gly Gly Trp Thr Ala
                245                 250                 255

Leu
```